United States Patent
Patil et al.

(10) Patent No.: US 11,865,108 B2
(45) Date of Patent: Jan. 9, 2024

(54) NITROGEN CONTAINING BICYCLIC COMPOUNDS

(71) Applicant: Wockhardt Limited, Aurangabad (IN)

(72) Inventors: Vijaykumar Jagdishwar Patil, Solapur (IN); Ravikumar Tadiparthi, Vijayawada (IN); Rajib Bhuniya, Burdwan (IN); Vikas Vitthalrao Deshmukh, Ahmednagar (IN); Zaki Ahmed Burhanuddin Munshi, Kalyan (IN); Piyush Ambalal Patel, Anand (IN); Prashant Ratnakar Joshi, Parbhani (IN); Rajesh Chavan, Aurangabad (IN); Swapna Shripad Takalkar, Aurangabad (IN); Ravindra Dattatraya Yeole, Aurangabad (IN); Mahesh Vithalbhai Patel, Aurangabad (IN)

(73) Assignee: Wockhardt Limited, Aurangabad (IN)

( * ) Notice: Subject to any disclaimer, the term of this patent is extended or adjusted under 35 U.S.C. 154(b) by 0 days.

(21) Appl. No.: 17/769,338

(22) PCT Filed: Oct. 18, 2020

(86) PCT No.: PCT/IN2020/050890
§ 371 (c)(1),
(2) Date: Apr. 15, 2022

(87) PCT Pub. No.: WO2021/074930
PCT Pub. Date: Apr. 22, 2021

(65) Prior Publication Data
US 2022/0378759 A1    Dec. 1, 2022

(30) Foreign Application Priority Data
Oct. 18, 2019  (IN) .............................. 201921042452

(51) Int. Cl.
*C07D 471/08*    (2006.01)
*A61K 31/439*    (2006.01)
*A61P 31/04*    (2006.01)
*A61K 31/546*    (2006.01)

(52) U.S. Cl.
CPC .......... *A61K 31/439* (2013.01); *A61K 31/546* (2013.01); *A61P 31/04* (2018.01); *C07D 471/08* (2013.01)

(58) Field of Classification Search
CPC ...... C07D 471/08; A61K 31/439; A61P 31/04
USPC .......................................... 546/121; 514/300
See application file for complete search history.

(56) References Cited

U.S. PATENT DOCUMENTS 9,732,081 B2 *   8/2017  Patil ................... A61K 31/4545

FOREIGN PATENT DOCUMENTS

| WO | 2014/033560 A1 | 3/2014 |
| WO | 2017/098425 A1 | 6/2017 |
| WO | 2018/158619 A1 | 9/2018 |

\* cited by examiner

*Primary Examiner* — Charanjit Aulakh
(74) *Attorney, Agent, or Firm* — N.V. Nederlandsch Octrooibureau

(57) ABSTRACT

Nitrogen containing bicyclic compounds of Formula (I), pharmaceutical compositions comprising these compounds and their use in treating bacterial infection is disclosed.

Formula (I)

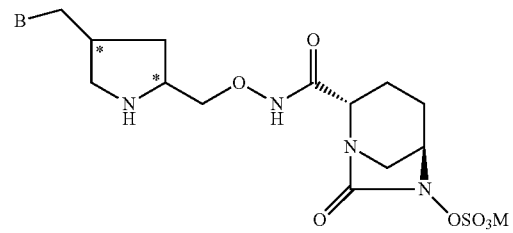

14 Claims, No Drawings

NITROGEN CONTAINING BICYCLIC COMPOUNDS

RELATED PATENT APPLICATIONS

This application claims the priority to and benefit of Indian Provisional Patent Application No. 201921042452 filed on Oct. 18, 2019; the disclosures of which are incorporated herein by reference in its entirety as if fully rewritten herein.

FIELD OF THE INVENTION

The invention relates to nitrogen containing bicyclic compounds, their preparation and their use in treating and/or preventing bacterial infections.

BACKGROUND OF THE INVENTION

The emergence of bacterial resistance to known antibacterial agents is becoming a major challenge in treating bacterial infections. One way forward to treat bacterial infections, and especially those caused by resistant bacteria, is to develop new antibacterial agents that can overcome the bacterial resistance. Coates et al. (*Br. J. Pharmacol.* 2007; 152(8), 1147-1154) have reviewed approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents. Several antibacterial agents have been described in the prior art. However, there remains a need for potent antibacterial agents for use in treatment and/or prevention of bacterial infections, including those caused by bacteria that have acquired resistance to one or more of the known antibacterial agents. The inventors have surprisingly discovered certain nitrogen containing bicyclic compounds having antibacterial properties.

SUMMARY OF THE INVENTION

Accordingly, there are provided nitrogen containing bicyclic compounds, methods for preparation of these compounds, pharmaceutical compositions comprising these compounds, and methods for treating and/or preventing bacterial infection in a subject using these compounds.

In one general aspect, there is provided a compound of Formula (I), or a stereoisomer or a pharmaceutically acceptable salt thereof;

Formula (I)

wherein:
B is selected from:
  (a) hydrogen,
  (b) halogen,
  (c) $C_1$-$C_6$ alkyl,
  (d)
  (e)
  (f) SH,
  (g)
  (h)
  (i)
  (j) CHO,
  (k)
  (l) $CONR_1R_2$,
  (m) CN,
  (n) heteroaryl,
  (o) heterocycloalkyl, or
  (p) $NHC(=NH)NH_2$;

$R_1$ and $R_2$ are each independently:
  (a) hydrogen,
  (b) $C_1$-$C_6$ alkyl, optionally substituted with one or more substituents independently selected from CN, halogen, OH, $NH_2$, COOH, $CONH_2$, SH, cycloalkyl, heterocycloalkyl, aryl, or heteroaryl,
  (c) three to seven membered cycloalkyl, optionally substituted with one or more substituents independently selected from CN, halogen, OH, $NH_2$, COOH, $CONH_2$, or SH,
  (d) three to seven membered heterocycloalkyl, optionally substituted with one or more substituents independently selected from CN, halogen, OH, $NH_2$, COOH, $CONH_2$, or SH,
  (e) six to fourteen membered aryl, optionally substituted with one or more substituents independently selected from CN, halogen, OH, $NH_2$, COOH, $CONH_2$, or SH, or
  (f) five to fourteen membered heteroaryl, optionally substituted with one or more substituents independently selected from CN, halogen, OH, $NH_2$, COOH, $CONH_2$, SH;

M is selected from:
  (a) hydrogen,
  (b) $C_1$-$C_6$ alkyl, or
  (c) a pharmaceutically accepted salt forming cation independently selected from Na, K, or Ca.

In another general aspect, there are provided pharmaceutical compositions comprising a compound of Formula (I), or a stereoisomer or a pharmaceutically acceptable salt thereof.

In another general aspect, there is provided a method for treating or preventing a bacterial infection in a subject, said method comprising administering to said subject a compound of Formula (I) or a stereoisomer or a pharmaceutically acceptable salt thereof.

In yet another general aspect, there is provided a method for treating or preventing a bacterial infection in a subject, said method comprising administering to said subject a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a process for preparing a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one of ordinary skills in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered certain nitrogen containing bicyclic compounds having antibacterial properties.

The term "$C_1$-$C_6$ alkyl" as used herein refers to branched or unbranched acyclic hydrocarbon radical with 1 to 6 carbon atoms. Typical, non-limiting examples of "$C_1$-$C_6$ alkyl" include methyl, ethyl, n-propyl, iso-propyl, n-butyl, iso-butyl, tert-butyl, n-pentyl, isopentyl, n-hexyl and the like. The "$C_1$-$C_6$ alkyl" may be unsubstituted, or substituted with one or more substituents. Typical, non-limiting examples of such substituents include halogen, alkoxy, CN, COOH, CONH$_2$, OH, —NH$_2$, —NHCOCH$_3$, cycloalkyl, heterocycloalkyl, heteroaryl, aryl, urea, thiourea, guanidine, keto, oxime, O-alkyl, O-aryl, N-alkyl, N-aryl, SO-alkyl, SO-aryl, S-alkyl, S-aryl, SO$_2$-alkyl, SO$_2$-aryl, OSO$_2$-alkyl, OSO$_2$-aryl, COO-alkyl, COO-aryl, CON-alkyl, CON-aryl, NHCO-alkyl, NHCO-aryl, NHCON-alkyl, NHCON-aryl, NHCSN-alkyl, NHC(=NH)NH$_2$, NHCSN-aryl, (=N—O-alkyl) and the like.

The term "cycloalkyl" as used herein refers to three to seven member cyclic hydrocarbon radicals. The cycloalkyl group optionally incorporates one or more double or triple bonds, or a combination of double bonds and triple bonds, but which is not aromatic. Typical, non-limiting examples of cycloalkyl groups include cyclopropane, cyclobutane, cyclopentane, cyclohexane, and cycloheptane. The cycloalkyl may be unsubstituted, or substituted with one or more substituents. Typical, non-limiting examples of such substituents include $C_1$-$C_6$ alkyl, halogen, CN, COOH, CONH$_2$, OH, —NH$_2$, —NHCOCH$_3$, cycloalkyl, heterocycloalkyl, heteroaryl, aryl, urea, thiourea, guanidine, keto, oxime, O-alkyl, O-aryl, N-alkyl, N-aryl, SO-alkyl, SO-aryl, S-alkyl, S-aryl, SO$_2$-alkyl, SO$_2$-aryl, OSO$_2$-alkyl, OSO$_2$-aryl COO-alkyl, COO-aryl, CON-alkyl, CON-aryl, NHCO-alkyl, NHCO-aryl, NHCON-alkyl, NHCON-aryl, NHCSN-alkyl, NHC(=NH)NH$_2$, NHCSN-aryl, (=N—O-alkyl) and the like.

The term "heterocycloalkyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include azetidine, pyrrolidine, 2-oxopyrrolidine, imidazolidin-2-one, piperidine, oxazine, thiazine, piperazine, morpholine, thiomorpholine, azapane, piperazin-2,3-dione and the like. The heterocycloalkyl may be unsubstituted, or substituted with one or more substituents. Typical, non-limiting examples of such substituents include $C_1$-$C_6$ alkyl, halogen, CN, COOH, CONH$_2$, OH, —NH$_2$, —NHCOCH$_3$, cycloalkyl, heterocycloalkyl, heteroaryl, aryl, urea, thiourea, guanidine, keto, oxime, O-alkyl, O-aryl, N-alkyl, N-aryl, SO-alkyl, SO-aryl, S-alkyl, S-aryl, SO$_2$-alkyl, SO$_2$-aryl, OSO$_2$-alkyl, OSO$_2$-aryl, COO-alkyl, COO-aryl, CON-alkyl, CON-aryl, NHCO-alkyl, NHCO-aryl, NHCON-alkyl, NHCON-aryl, NHCSN-alkyl, NHC(=NH)NH$_2$, NHCSN-aryl, (=N—O-alkyl) and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like. The aryl group may be unsubstituted, or substituted with one or more substituents. Typical, non-limiting examples of such substituents include $C_1$-$C_6$ alkyl, halogen, CN, COOH, CONH$_2$, OH, —NH$_2$, —NHCOCH$_3$, cycloalkyl, heterocycloalkyl, heteroaryl, aryl, urea, thiourea, guanidine, keto, oxime, O-alkyl, O-aryl, N-alkyl, N-aryl, SO-alkyl, SO-aryl, S-alkyl, S-aryl, SO$_2$-alkyl, SO$_2$-aryl, OSO$_2$-alkyl, OSO$_2$-aryl, COO-alkyl, COO-aryl, CON-alkyl, CON-aryl, NHCO-alkyl, NHCO-aryl, NHCON-alkyl, NHCON-aryl, NHCSN-alkyl, NHCSN-aryl, NHC(=NH)NH$_2$, (=N—O-alkyl) and the like.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include 1,2,4-oxadiazol, 1,3,4-oxadiazol, 1,3,4-thiadiazol, 1,2,3-triazol, 1,2,3,4-tetrazol, 1,3-oxazol, 1,3-thiazole, pyridine, pyrimidine, pyrazine, pyridazine, furan, pyrrol, thiophene, imidazole, pyrazole, benzofuran, benzothiophene, benzimidazole, benzoxazole, benzothiazole, thiazole, and the like. The heteroaryl group may be unsubstituted, or substituted with one or more substituents. Typical, non-limiting examples of such substituents include $C_1$-$C_6$ alkyl, halogen, CN, COOH, CONH$_2$, OH, —NH$_2$, —NHCOCH$_3$, cycloalkyl, heterocycloalkyl, heteroaryl, aryl, urea, thiourea, guanidine, keto, oxime, O-alkyl, O-aryl, N-alkyl, N-aryl, SO-alkyl, SO-aryl, S-alkyl, S-aryl SO$_2$-alkyl, SO$_2$-aryl, OSO$_2$-alkyl, OSO$_2$-aryl, COO-alkyl, COO-aryl, CON-alkyl, CON-aryl, NHCO-alkyl, NHCO-aryl, NHCON-alkyl, NHCON-aryl, NHCSN-alkyl, NHC(=NH)NH$_2$, NHCSN-aryl, (=N—O-alkyl) and the like.

The term "stereoisomers" as used herein refers to and includes compounds that have identical chemical constitution, but differ with regard to the arrangement of their atoms or groups in space. The compounds of Formula (I) contains asymmetric or chiral centres (including those marked with "*") and, therefore, exist in different stereoisomeric forms. It is intended, unless specified otherwise, that all stereoisomeric forms of the compounds of Formula (I) as well as mixtures thereof, including racemic mixtures, form part of the present invention. In addition, all geometric and positional isomers (including cis and trans-forms) as well as mixtures thereof, are also embraced within the scope of the invention. In general, a reference to a compound is intended to cover its stereoisomers and a mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valence of the designated atom or moiety is not exceeded, and that the substitution results in a stable compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to and include those salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

In general, the compounds according to the invention contain basic (e.g. nitrogen atoms) as well as acid moieties (e.g. $SO_3H$ group). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to a salt independently. For example, in case of compounds containing two basic nitrogen atoms, one of the basic nitrogen can form salt with one acid while the other basic nitrogen can form salt with another acid. The compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "infection" or "bacterial infection" as used herein refers to and includes presence of bacteria, in or on a subject, which, if its growth were inhibited, would result in a benefit to the subject. As such, the term "infection" in addition to referring to the presence of bacteria also refers to normal flora, which is not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection. The compounds and/or pharmaceutical compositions according to the invention are used in amounts that are effective in providing the desired therapeutic effect or result.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intra-respiratory, intra-peritoneal, intra-muscular, parenteral, sublingual, transdermal, intranasal, aerosol, intra-ocular, intra-tracheal, intra-rectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or the desired effect.

The term "growth" as used herein refers to a growth of one or more microorganisms and includes reproduction or population expansion of the microorganism (e.g. bacteria). The term "growth" also includes maintenance of on-going metabolic processes of a microorganism (e.g. bacteria), including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to treat or prevent the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyse the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to a vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

In one general aspect, there is provided a compound of Formula (I), or a stereoisomer or a pharmaceutically acceptable salt thereof;

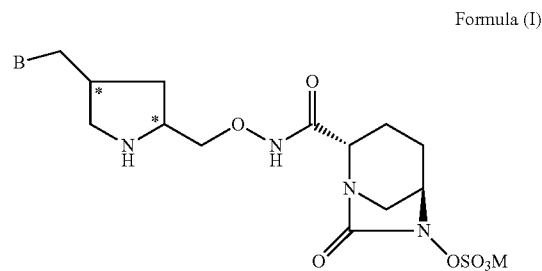

Formula (I)

wherein:

B is selected from:
(a) hydrogen,
(b) halogen,
(c) $C_1$-$C_6$ alkyl,
(d) $OR_1$,
(e) $NR_1R_2$,
(f) SH,
(g) $SR_1$,
(h) $SOR_1$,
(i) $SO_2R_1$,
(j) CHO,
(k) $COOR_1$,
(l) $CONR_1R_2$,
(m) CN,
(n) heteroaryl,
(o) heterocycloalkyl, or
(p) NHC(=NH)$NH_2$;

$R_1$ and $R_2$ are each independently:
(a) hydrogen,
(b) $C_1$-$C_6$ alkyl, optionally substituted with one or more substituents independently selected from CN, halogen, OH, $NH_2$, COOH, $CONH_2$, SH, cycloalkyl, heterocycloalkyl, aryl, or heteroaryl,
(c) three to seven membered cycloalkyl, optionally substituted with one or more substituents independently selected from CN, halogen, OH, $NH_2$, COOH, $CONH_2$, or S11,
(d) three to seven membered heterocycloalkyl, optionally substituted with one or more substituents independently selected from CN, halogen, OH, $NH_2$, COOH, $CONH_2$, or SH,
(e) six to fourteen membered aryl, optionally substituted with one or more substituents independently selected from CN, halogen, OH, $NH_2$, COOH, $CONH_2$, or SH, or
(f) five to fourteen membered heteroaryl, optionally substituted with one or more substituents independently selected from CN, halogen, OH, $NH_2$, COOH, $CONH_2$, SH;

M is selected from:
(a) hydrogen,
(b) $C_1$-$C_6$ alkyl, or
(c) a pharmaceutically accepted salt forming cation independently selected from Na, K, or Ca.

Typical, non-limiting examples of compounds according to the invention include:
(2S,5R)—N-{[(2S,4R)-4-Methyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Methyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Methyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Hydroxymethyl-pyrrolidin-2-yl]methyloxy}-7-oxo-6-(sulfooxy)-1,6-diazabicyclo[3.2.1]octane-2-carboxamide;

2S,5R)—N-{[(2S,4S)-4-Hydroxymethy-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Hydroxymethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Hydroxymethy-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;

(2S,5R)—N-{[(2S,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;

(2S,5R)—N-{[(2R,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;

(2S,5R)—N-{[(2R,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;

(2S,5R)—N-{[(2S,4R)-4-Cyanomethyl-pyrrolidin-2-yl]methyloxy}-7-oxo-6-(sulfooxy)-1,6-diazabicyclo[3.2.1]octane-2-carboxamide;

2S,5R)—N-{[(2S,4S)-4-Cyanomethy-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Cyanomethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Cyanomethy-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-1,2,4,triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(2H-tetrazoly-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,4S)-4-Carbamimidomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Carbamimidomethyl-pyrrolidin-2-yl]methyloxy}-7-oxo-6-(sulfooxy)-1,6-diazabicyclo[3.2.1]octane-2-carboxamide;
(2S,5R)—N-{[(2R,4S)-4-Carbamimidomethyl-pyrrolidin-2-yl]methyloxy}-7-oxo-6-(sulfooxy)-1,6-diazabicyclo[3.2.1]octane-2-carboxamide;
(2S,5R)—N-{[(2R,4R)-4-Carbamimidomethyl-pyrrolidin-2-yl]methyloxy}-7-oxo-6-(sulfooxy)-1,6-diazabicyclo[3.2.1]octane-2-carboxamide;
or a stereoisomer or a pharmaceutically acceptable salt thereof.

In some embodiments, typical, non-limiting examples of compounds according to the invention include:
Sodium salt of (2S,5R)—N-{[(2S,4R)-4-Methyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Methyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Methyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Hydroxymethyl-pyrrolidin-2-yl]methyloxy}-7-oxo-6-(sulfooxy)-1,6-diazabicyclo[3.2.1]octane-2-carboxamide;
Sodium salt of 2S,5R)—N-{[(2S,4S)-4-Hydroxymethy-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Hydroxymethy-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Hydroxymethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;
Sodium salt of (2S,5R)—N-{[(2S,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;
Sodium salt of (2S,5R)—N-{[(2R,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;
Sodium salt of (2S,5R)—N-{[(2R,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;
Sodium salt of (2S,5R)—N-{[(2S,4R)-4-Cyanomethyl-pyrrolidin-2-yl]methyloxy}-7-oxo-6-(sulfooxy)-1,6-diazabicyclo[3.2.1]octane-2-carboxamide;
Sodium salt of 2S,5R)—N-{[(2S,4S)-4-Cyanomethy-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Cyanomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Cyanomethy-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Fluoromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-Fluoromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Fluoromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Fluoromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Chloromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-Chloromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Chloromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Chloromethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Mercaptomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-Mercaptomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Mercaptomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Mercaptomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Azepan-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Azepan-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Azepan-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Azepan-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-1,2,4,triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-tetrazol-1-yl-methyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(2H-tetrazoly-2-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(2H-tetrazol-2-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(2H-tetrazol-2-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(2H-tetrazol-2-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-Carbamimidom-ethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Carbamimidom-ethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Carbamimidom-ethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Carbamimidom-ethyl-pyrrolidin-2-yl]methyloxy}-7-oxo-6-(sulfooxy)-1,6-diazabicyclo[3.2.1]octane-2-carboxamide;

or a stereoisomer thereof.

Typical, non-limiting examples of compounds according to the invention include:

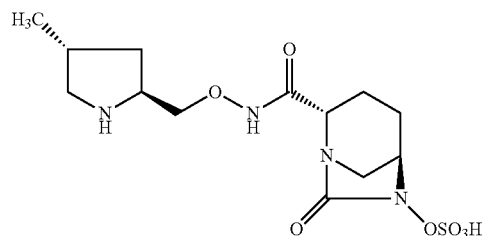

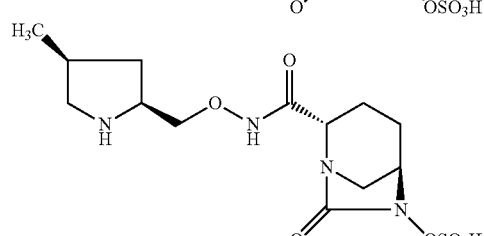

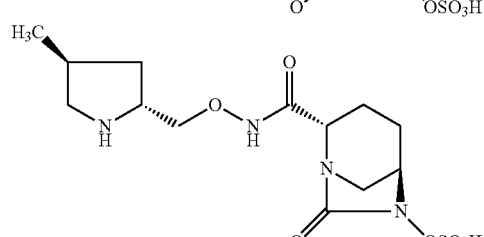

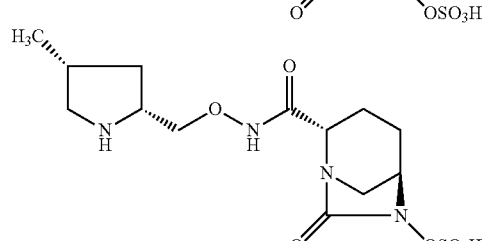

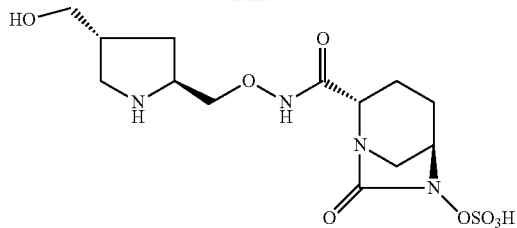

-continued

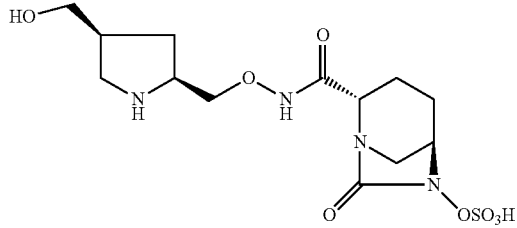

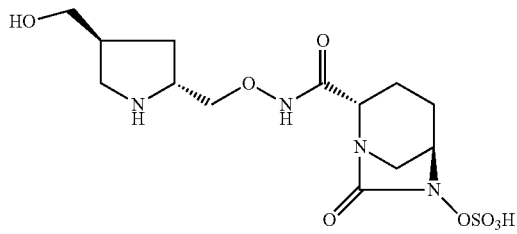

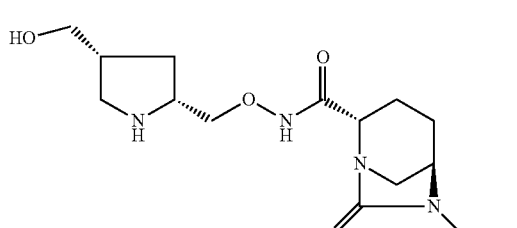

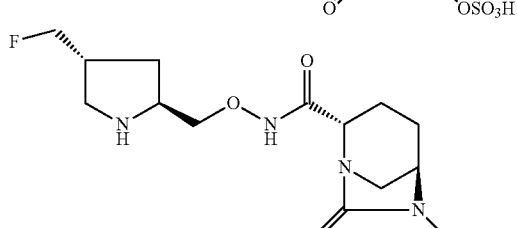

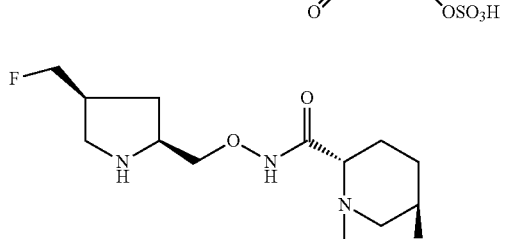

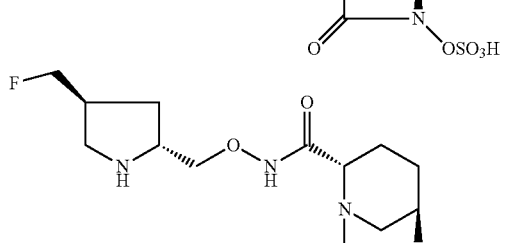

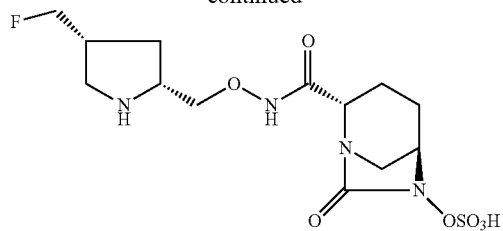
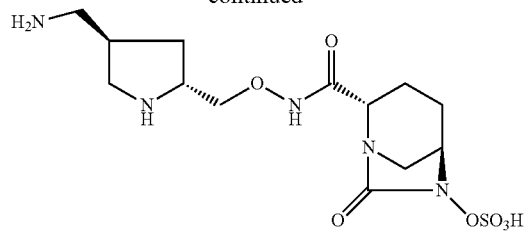
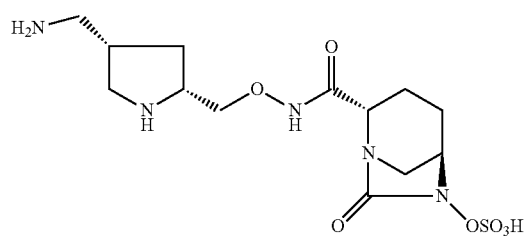
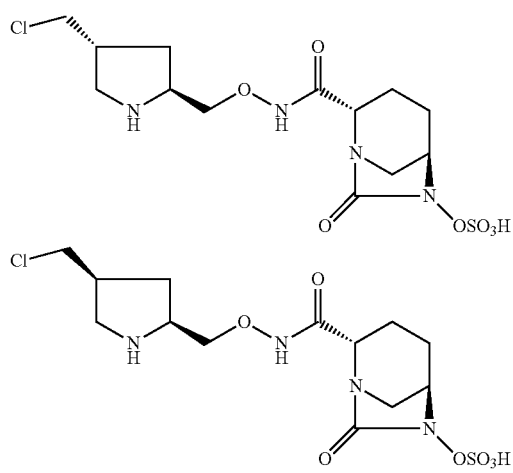
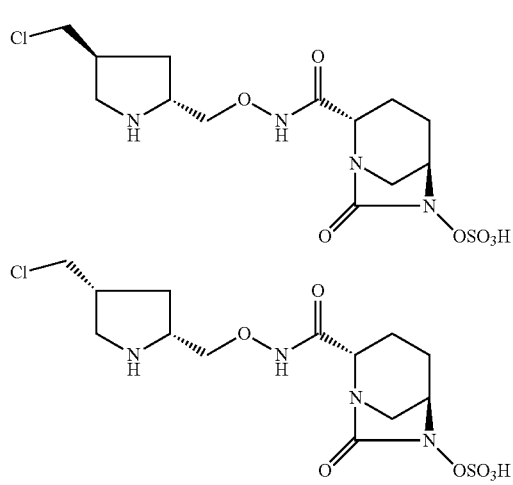
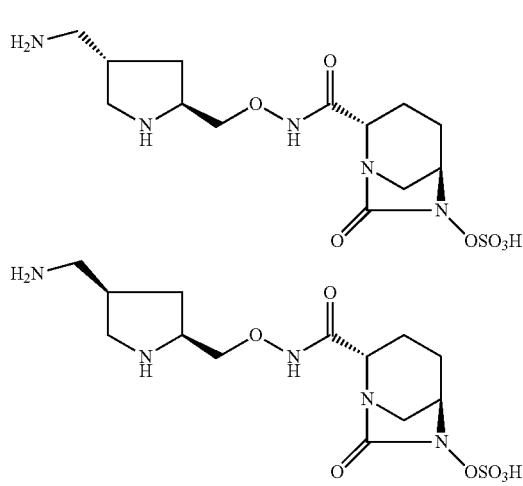

-continued
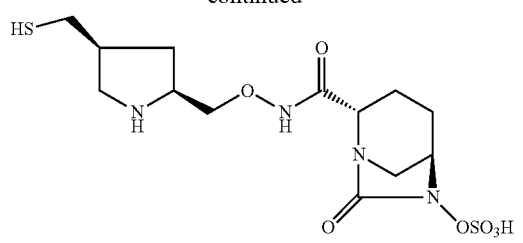
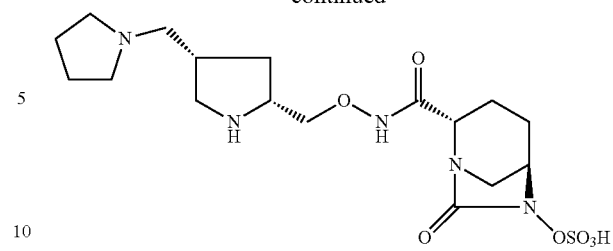
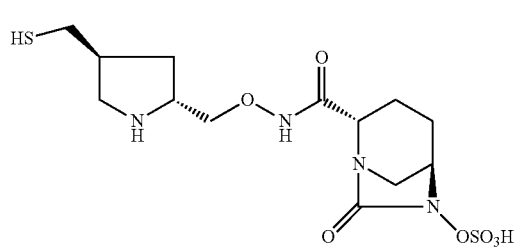
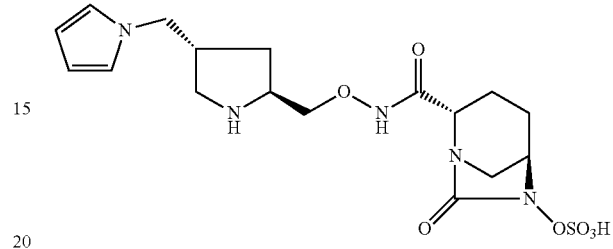
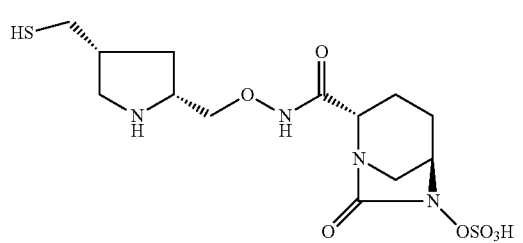
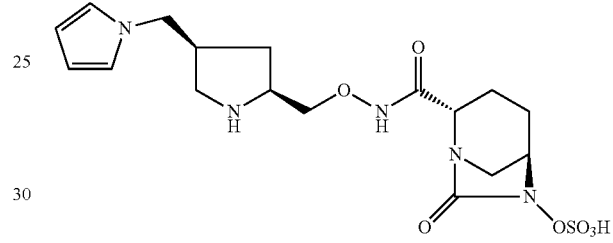
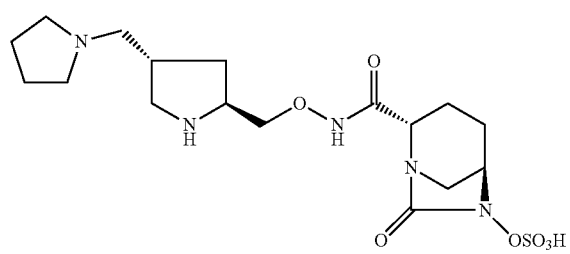
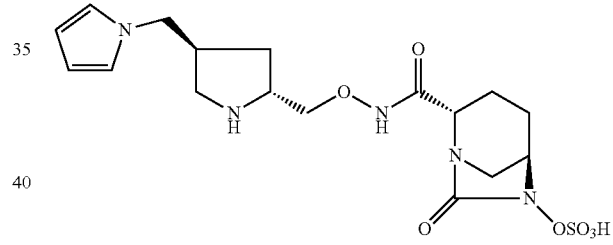
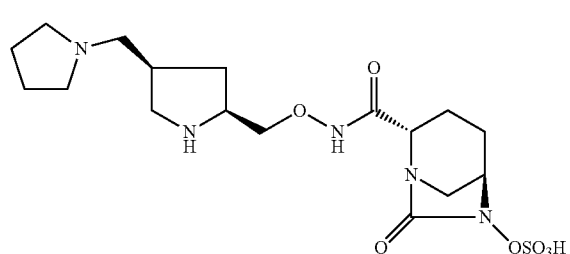
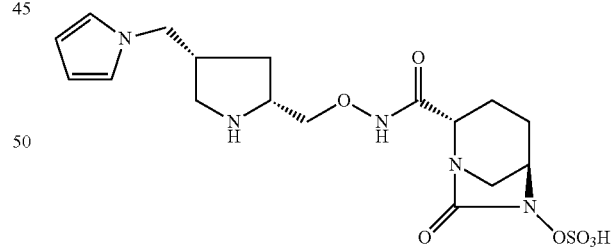
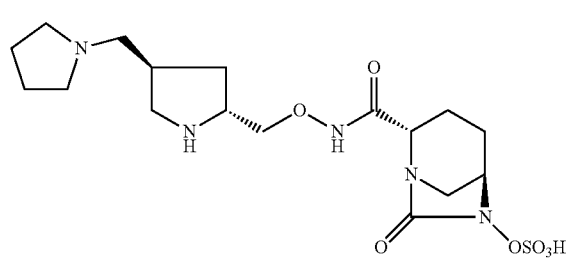
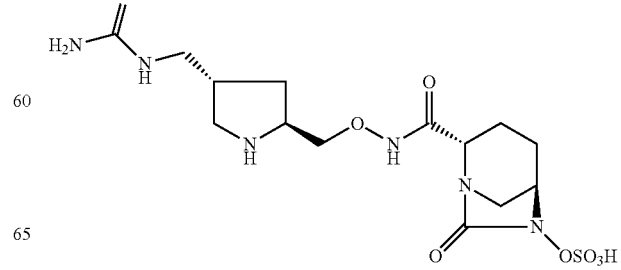

23
-continued

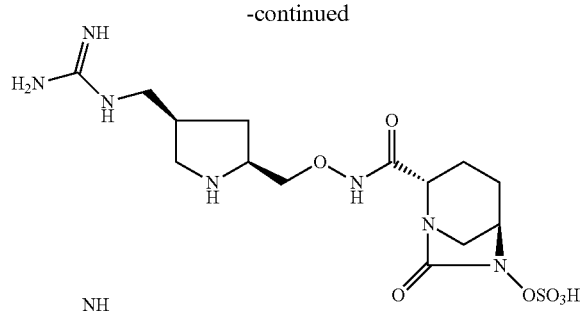

24
-continued

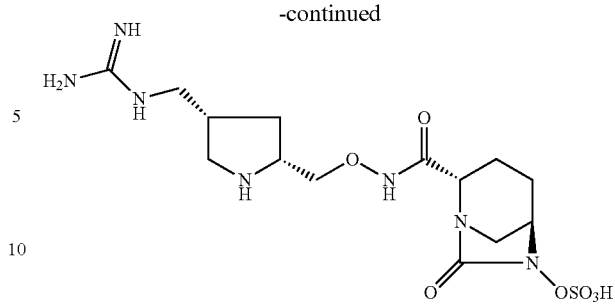

The compounds of the invention can be prepared according to the general procedure given in Scheme 1 and Scheme 2. Individual stereoisomers can be prepared using appropriate starting materials and reagents. A person of skills in the art would appreciate that the described methods can be varied and/or optimized further to provide the desired and related compounds.

Scheme 1

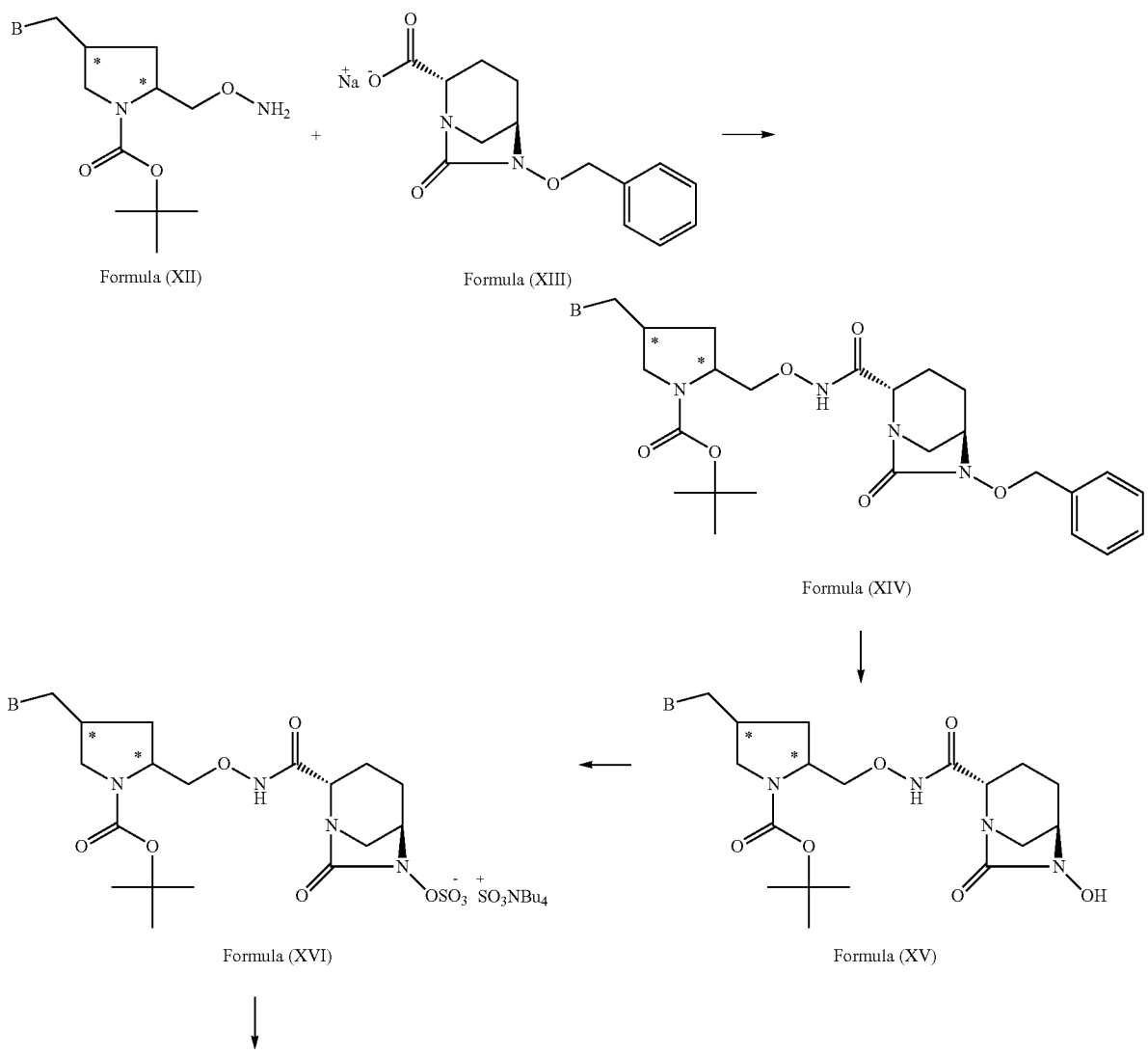

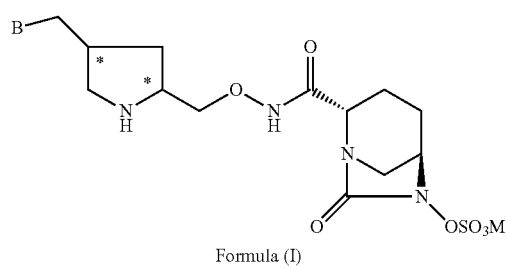
-continued
Formula (I)
Scheme 2
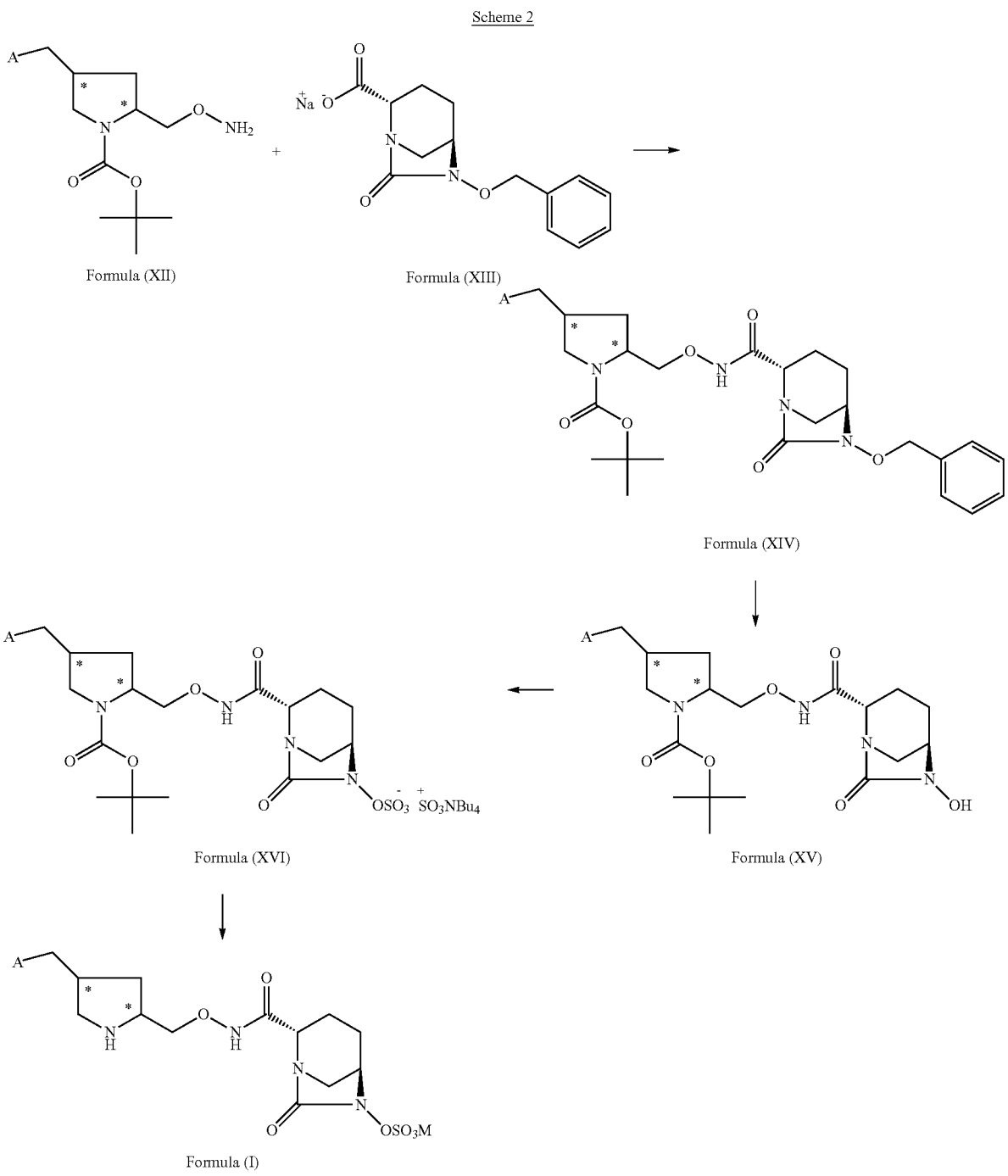

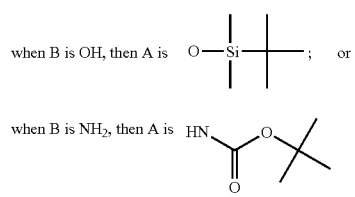

Typically, a compound of Formula (XII) is reacted with a sodium salt of (2S,5R)-6-benzyloxy-7-oxo-1,6-diaza-bicyclo[3.2.1]octane-2-carboxylic acid (XIII) to obtain a compound of Formula (XIV). The compound of Formula (XIV) is then converted into a compound of Formula (XV) in presence of a suitable debenzylating agent. Typical, not-limiting examples of suitable debenzylating agents include hydrogen gas in presence of a transition metal catalyst such as palladium on carbon. The compound of Formula (XV) is converted into a compound of Formula (XVI) in presence of a suitable sulfonating agent. Typical, not-limiting examples of suitable sulfonating agents include sulfur trioxide dimethylformamide complex. The sulfonation reaction is followed by treatment with tetrabutylammonium acetate to obtain a compound of Formula (XVI). The compound of Formula (XVI) is converted into a compound of Formula (I) in presence of a suitable de-protecting agent. Typical, not-limiting examples of suitable de-protecting agents include trifluoroacetic acid. A wide variety of other reagents which can bring about these functional transformations can also be used.

More specifically some compounds according to the invention were isolated as a zwitterions, by treating intermediate compound (XVI) with trifluoroacetic acid, in a suitable solvent (such as dichloromethane, chloroform, or acetonitrile) at a temperature ranging from about −10° C. to −15° C. for about 1 to 14 hours, especially when A in intermediate compound (XVI) contained tert-butoxycarbonyl protected amine function.

Some compounds according to the invention were isolated as a zwitterions, by treating intermediate compound (XVI) with tetrabutyl ammonium fluoride followed by trifluoroacetic acid, in a suitable solvent, especially when A in intermediate compound (XVI) contained tert-butyldimethylsilyl (TBDMS) protected hydroxy function and tert-butoxycarbonyl (BOC) protected amine function Some other compounds according to the invention were isolated as a corresponding sodium salt, by passing intermediate compound (XVI) through appropriate sodium ion exchange resin in a tetrahydrofuran-water mixture followed by evaporation of the solvent under vacuum.

In some embodiments, there are provided pharmaceutical compositions comprising a compound of Formula (I), or a stereoisomer or a pharmaceutically acceptable salt thereof.

In some embodiments, there are provided pharmaceutical compositions comprising a compound which is (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there are provided pharmaceutical compositions comprising a compound which is (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In some embodiments, there are provided pharmaceutical compositions comprising: (a) (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, and (b) at least one antibacterial agent or a pharmaceutically acceptable derivative thereof.

In some embodiments, there are provided pharmaceutical compositions comprising: (a) (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, and (b) at least one antibacterial agent or a pharmaceutically acceptable derivative thereof.

In some embodiments, there are provided pharmaceutical compositions comprising: (a) (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, and (b) one or more of cefixime, cefpodoxime, ceftibuten, cefuroxime, or a pharmaceutically acceptable salt thereof.

In some embodiments, there are provided pharmaceutical compositions comprising: (a) ((2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, and (b) one or more of cefixime, cefpodoxime, ceftibuten, cefuroxime, or a pharmaceutically acceptable salt thereof.

In some other embodiments, there are provided methods for treating or preventing a bacterial infection in a subject, said method comprising administering to said subject, compounds or pharmaceutical compositions according to the invention.

In some other embodiments, there are provided methods for treating or preventing bacterial infection in a subject, said method comprising administering to said subject a compound of Formula (I), or a stereoisomer or a pharmaceutically acceptable salt thereof.

In some embodiments, there are provided methods for treating or preventing bacterial infection in a subject, said method comprising administering to said subject a pharmaceutical composition comprising a compound of Formula (I) or a stereoisomer or a pharmaceutically acceptable salt thereof.

In some embodiments, the compounds and/or the compositions according to the invention are used in treating or preventing bacterial infection.

In some embodiments, there is provided for use of a compound which is (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, in treating or preventing a bacterial infection.

In some embodiments, there is provided for use of a compound which is (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, in treating or preventing a bacterial infection.

In some embodiments, a compound which is (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, is used in the preparation of a medicament for treating or preventing a bacterial infection.

In some embodiments, a compound which is (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof, is used in the preparation of a medicament for treating or preventing a bacterial infection.

In some embodiments, there is provided a method for treating or preventing bacterial infection in a subject, said method comprising administering to said subject a compound which is (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there is provided a method for treating or preventing bacterial infection in a subject, said method comprising administering to said subject a compound which is (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there is provided a method for treating or preventing bacterial infection in a subject, said method comprising administering to said subject a pharmaceutical composition comprising (2S,5R)—N-{[(2S,4R)-4-methylpyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there is provided a method for treating or preventing bacterial infection in a subject, said method comprising administering to said subject a pharmaceutical composition comprising (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

The compositions and methods according to the invention use compounds of Formula (I) or a stereoisomer or a pharmaceutically acceptable salt thereof, in combination with at least one antibacterial agent or a pharmaceutically acceptable derivative thereof. A wide variety of antibacterial agents can be used in combination with the compounds according to the invention. The antibacterial agents are often classified depending on their structure or mode of action.

Typical, non-limiting examples of antibacterial agents include those belonging to a group of antibacterial agents such as Ansamycins, Carbacephems, Carbapenams, Carbapenems, Cephalosporins, Cephamycins, Cephems, Lincosamides, Lipopeptides, Macrolides, Ketolides, Monobactams, Nitrofurans, Oxacephems, Oxapenams, Oxazolidinones, Penams, Penems, Penicillins, Polypeptides, Quinolones, Sulfonamides, Tetracyclines, and a like.

In some embodiments, the antibacterial agent is a beta-lactam antibacterial agent.

Typical, non-limiting, examples of a beta-lactam antibacterial agents include those generally known as Carbacephems, Carbapenams, Carbapenems, Cephalosporins, Cephamycins, Cephems, Monobactams, Oxacephems, Oxapenams, Penams, Penems, Penicillins and a like.

Typical, non-limiting, examples of antibacterial agents include cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefclidin, cefdaloxime, cefdinir, cefditoren, cefepime, cefetamet, cefixime, cefluprenam, cefmenoxime, cefmetazole, cefminox, cefodizime, cefonicid, cefoperazone, ceforanide, cefoselis, cefotaxime, cefotetan, cefotiam, cefovecin, cefoxitin, cefoxitin, cefozopran, cefpimizole, cefpiramide, cefpirome, cefpodoxime, cefprozil, cefquinome, cefradine, cefroxadine, cefsulodin, ceftaroline, ceftazidime, cefteram, ceftezole, ceftibuten, ceftiofur, ceftiolene, ceftizoxime, ceftobiprole, ceftolozane, ceftriaxone, cefuroxime, cefuzonam, cephaloridine, cephradine, ceftolozane (CXA-101), cefiderocol, flomoxef, latamoxef, loracarbef, moxalactam and a like.

In some embodiments, the antibacterial agent is at least one selected from cefaclor, cefadroxil, cefalexin, cefdinir, cefixime, cefpodoxime, cefprozil, cefradine, ceftibuten, cefuroxime, loracarbef or a pharmaceutically acceptable derivative thereof.

In some embodiments, the antibacterial agent is at least one selected from cefpodoxime axetil, cefpodoxime proxetil, ceftibuten, cefuroxime, cefuroxime axetil, cefixime, or a pharmaceutically acceptable derivative thereof.

Typical, non-limiting examples of Aminoglycoside antibacterial agents include amikacin, gentamicin, kanamycin, neomycin, netilmicin, tobramycin, paromomycin, arbekacin, streptomycin, apramycin, plazomicin and a like.

Typical, non-limiting examples of Ansamycin antibacterial agents include geldanamycin, herbimycin and a like.

Typical, non-limiting examples of Carbapenem antibacterial agents include ertapenem, doripenem, imipenem, meropenem, panipenem, biapenem, tebipenem, lenapenem, tomopenem and a like.

Typical, non-limiting examples of Lincosamide antibacterial agents include clindamycin, lincomycin and a like.

Typical, non-limiting examples of Macrolide antibacterial agents include azithromycin, clarithromycin, dirithromycin, erythromycin, roxithromycin, troleandomycin, telithromycin, spectinomycin, solithromycin, nafithromycin and a like.

Typical, non-limiting examples of Monobactams antibacterial agents include aztreonam, tigemonam, carumonam, nocardicin A, LYS-228, AIC499, sulfazecin, monosulfactam 0073, tabtoxin and a like.

Typical, non-limiting examples of Nitrofuran antibacterial agents include furazolidone, nitrofurantoin and a like.

Typical, non-limiting examples of Penicillin antibacterial agents include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin and a like.

Typical, non-limiting examples of Polypeptide antibacterial agents include bacitracin, colistin, polymyxin B and a like.

Typical, non-limiting examples of pleuromutilin antibiotic include lefamulin and a like.

Typical, non-limiting examples of Quinolone antibacterial agents include ciprofloxacin, enoxacin, gatifloxacin, levofloxacin, lomefloxacin, moxifloxacin, nalidixic acid, levonadifloxacin, norfloxacin, ofloxacin, trovafloxacin, grepafloxacin, sparfloxacin, temafloxacin, fleroxacin, pefloxacin, sitafloxacin and a like.

Typical, non-limiting examples of Sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and a like.

Typical, non-limiting examples of Tetracycline antibacterial agents include demeclocycline, doxycycline, minocycline, oxytetracycline, tetracycline, tigecycline and a like.

Typical, non-limiting examples of Oxazolidinone antibacterial agents include tedizolid, linezolid, ranbezolid, torezolid, radezolid, (5S)—N-{3-[3,5-difluoro-4-(4-hydroxy-(4-methoxymethyl)-piperidin-1-yl)phenyl]-2-oxo-oxazolidin-5-ylmethyl}-acetamide and a like.

In general, the compounds, pharmaceutical compositions and method disclosed herein are useful in treating and/or preventing bacterial infections. Advantageously, the compounds, compositions and methods disclosed herein are also effective in treating or preventing infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be treated or prevented using the compounds, compositions and/or methods according to the invention include: skin and soft tissue infections, febrile neutropenia, urinary tract infection, intraabdominal infections, respiratory tract infections, pneumonia (nosocomial), bacteremia meningitis, surgical infections etc.

Surprisingly, the compounds, compositions and methods according to the invention are also effective in treating and/or preventing bacterial infections that are caused by bacteria producing one or more beta-lactamase enzymes. The ability of the compounds, compositions and/or methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of an antibacterial agent in a subject. The antibacterial effectiveness of one or more antibacterial agents may be increased, for example, by co-administering said antibacterial agent or a pharmaceutically acceptable derivative thereof with a compound of Formula (I) or a stereoisomer or a pharmaceutically acceptable salt thereof according to the invention.

In some embodiments, there is provided a process for preparation of a compound of Formula (I), or a stereoisomer or a pharmaceutically acceptable salt thereof;

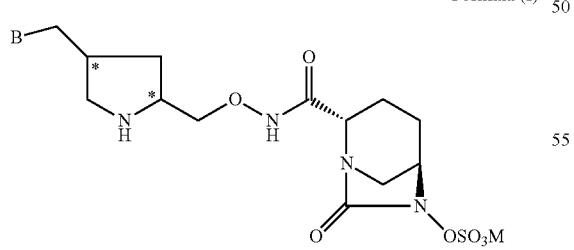

Formula (I)

wherein:
B is selected from:
(a) hydrogen,
(b) halogen,
(c) $C_1$-$C_6$ alkyl,
(d) $OR_1$,
(e) $NR_1R_2$,
(f) SH,
(g) $SR_1$,
(h) $SOR_1$,
(i) $SO_2R_1$,
(j) CHO,
(k) $COOR_1$,
(l) $CONR_1R_2$,
(m) CN,
(n) heteroaryl,
(o) heterocycloalkyl, or
(p) NHC(=NH)$NH_2$;

$R_1$ and $R_2$ are each independently:
(a) hydrogen,
(b) $C_1$-$C_6$ alkyl, optionally substituted with one or more substituents independently selected from CN, halogen, OH, $NH_2$, COOH, $CONH_2$, SH, cycloalkyl, heterocycloalkyl, aryl, or heteroaryl,
(c) three to seven membered cycloalkyl, optionally substituted with one or more substituents independently selected from CN, halogen, OH, $NH_2$, COOH, $CONH_2$, or SH,
(d) three to seven membered heterocycloalkyl, optionally substituted with one or more substituents independently selected from CN, halogen, OH, $NH_2$, COOH, $CONH_2$, or SH,
(e) six to fourteen membered aryl, optionally substituted with one or more substituents independently selected from CN, halogen, OH, $NH_2$, COOH, $CONH_2$, or SH, or
(f) five to fourteen membered heteroaryl, optionally substituted with one or more substituents independently selected from CN, halogen, OH, $NH_2$, COOH, $CONH_2$, SH;

M is selected from:
(a) hydrogen,
(b) $C_1$-$C_6$ alkyl, or
(c) a pharmaceutically accepted salt forming cation independently selected from Na, K, or Ca.

Comprising:
(a) reacting a compound of Formula (XII) with a compound of Formula (XIII) to obtain a compound of Formula (XIV);

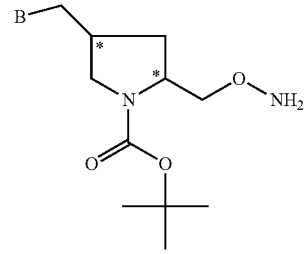

Formula (XII)

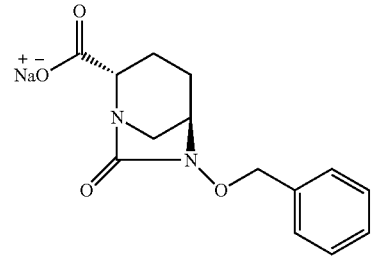

Formula (XIII)

-continued

Formula (XIV)

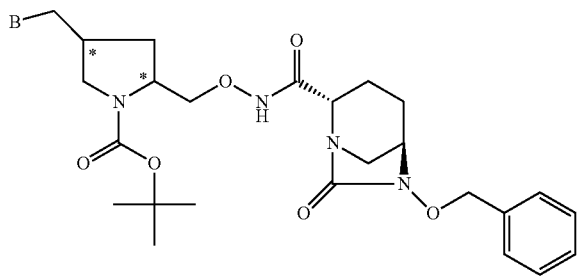

(b) converting a compound of Formula (XIV) into a compound of Formula (XV);

Formula (XV)

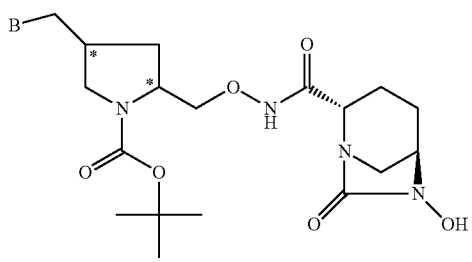

(c) converting a compound of Formula (XV) into a compound of Formula (XVI); and

Formula (XVI)

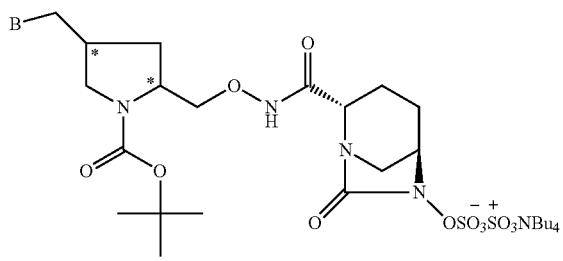

(d) converting a compound of Formula (XVI) into a compound of Formula (I).

In some embodiments, the compound of Formula (XIV) is obtained by reacting a compound of Formula (XII) with sodium salt of (2S,5R)-6-benzyloxy-7-oxo-1,6-diazabicyclo[3.2.1]octane-2-carboxylic acid (XIII) in presence of suitable reagents. Typical, non-limiting examples of these reagents include 1-hydroxybenzotriazole (HOBt), 1-ethyl-3-(3-dimethylaminopropyl)carbodiimide hydrochloride (EDC.HCl) and N-Methyl Morpholine (NMM).

In some other embodiments, the compound of Formula (XIV) is converted into a compound of Formula (XV) in presence of a suitable debenzylating agent. Typical, not-limiting examples of suitable debenzylating agents include hydrogen gas in presence of a transition metal catalyst such as palladium on carbon.

In some other embodiments, the compound of Formula (XV) is converted into a compound of Formula (XVI) in presence of a suitable sulfonating agent followed by a treatment with tetrabutylammonium acetate. Typical, not-limiting examples of suitable sulfonating agents include sulfur trioxide dimethylformamide complex. The sulfonation reaction is followed by treatment with tetrabutylammonium acetate to obtain a compound of Formula (XVI).

In some other embodiments, the compound of Formula (XVI) is converted into a compound of Formula (I) in presence of a suitable deprotecting agent. Typical, not-limiting examples of suitable deprotecting agents include trifluoroacetic acid.

More specifically some compounds according to the invention were isolated as a zwitterions, by treating intermediate compound (XVI) with trifluoroacetic acid, in a suitable solvent (such as dichloromethane, chloroform, or acetonitrile) at a temperature ranging from about −10° C. to −15° C. for about 1 to 14 hours, especially when A in intermediate compound (XVI) contained tert-butoxycarbonyl protected amine function.

Some compounds according to the invention were isolated as a zwitterions, by treating intermediate compound (XVI) with tetrabutyl ammonium fluoride followed by trifluoroacetic acid, in a suitable solvent, especially when A in intermediate compound (XVI) contained tert-butyldimethylsilyl (TBDMS) protected hydroxy function and tert-butoxycarbonyl (BOC) protected amine function Some other compounds according to the invention were isolated as a corresponding sodium salt, by passing intermediate compound (XVI) through appropriate sodium ion exchange resin in a tetrahydrofuran-water mixture followed by evaporation of the solvent under vacuum.

A wide variety of other reagents which can bring about these functional transformations can be used. It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

(2S,5R)—N-{[(2S,4R)-4-methylpyrrolidin-2-yl]methyloxy}-7-oxo-6-(sulfooxy)-1,6-diazabicyclo[3.2.1]octane-2-carboxamide (Ia)

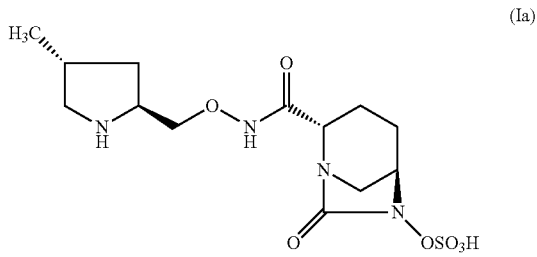

Step 1: Synthesis of 1-tert-butyl 2-methyl (2S,4R)-4-[(methylsulfonyloxy) methyl]pyrrolidine-1,2-dicarboxylate (VIIa)

To a solution of 1-tert-butyl 2-methyl (2S,4R)-4-hydroxymethyl pyrrolidine-1,2-dicarboxylate (VIa) (5.0 g, 19.28 mmol; prepared by following similar procedures described in published PCT international application with publication number WO 2013/075029A1) in 50 mL dichloromethane was added triethylamine (4.29 mL, 30.55 mmol) in one lot and the resulting solution was cooled up to −10° C. To this cooled solution methanesulfonyl chloride (2.65 g, 23.13 mmol) was added drop-wise under stirring. The reaction was monitored by Thin Layer Chromatography (TLC) (ethyl acetate:Hexane 1:1). After complete consumption of starting material, water (50 mL) was added to the reaction mixture and stirred further for 0.5 hour. The organic layer was separated, washed with water (20 mL) and dried over sodium sulphate. The solvent was evaporated under reduced pressure to obtain yellowish residue. The residue was dried under high vacuum and used as such for the next reaction without any further purification (6.5 g, yield 99%).

Analysis:
Mass: 338.2 (M+H) for M.W: 337.39; M.F: $C_{13}H_{23}NO_7S$

Step-2: Synthesis of 1-tert-butyl 2-methyl (2S,4R)-4-iodomethylpyrrolidine-1,2-dicarboxylate (VIIIa)

To a solution of 1-tert-butyl 2-methyl (2S,4R)-4-[(methylsulfonyloxy) methyl] pyrrolidine-1,2-dicarboxylate (VIIa) (6.50 g, 19.26 mmol) in acetone (65 mL) was added sodium iodide (7.65 g, 51.04 mmol), at 25° C. The reaction mixture was refluxed. The reaction was monitored by TLC (ethyl acetate:hexane 1:1). After complete consumption of starting material the reaction mixture was filtered under suction and the residue obtained was washed with additional acetone (20 mL). The combined filtrates were evaporated under reduced pressure and the residue obtained was dissolved in 100 ml of ethyl acetate. The ethyl acetate layer was washed with 100 ml, 5% aq. sodium thiosulphate solution followed by 50 ml saturated brine solution. The ethyl acetate layer was dried over sodium sulfate and the solvent evaporated under reduced pressure to obtain yellowish oil as residue. The residue was dried under high vacuum to obtain 1-tert-butyl 2-methyl (2S,4R)-4-iodomethylpyrrolidine-1, 2-dicarboxylate (VIIIa) (6.0 g, yield 84.0%) and used as such in the next reaction without any further purification Analysis:
Mass: 370.5 (M+H) for M.W: 369.20; M.F: $C_{12}H_{20}INO_4$

Step-3: Synthesis of 1-tert-butyl 2-methyl (2S,4R)-4-methylpyrrolidine-1, 2-dicarboxylate (IXa)

To a solution of 1-tert-butyl 2-methyl (2S,4R)-4-iodomethylpyrrolidine-1, 2-dicarboxylate (VIIIa) (6.0 g, 16.89 mmoles) in methanol (60 mL) was added 10% Pd/C (0.6 g). The solution was hydrogenated in 50 psi at 25-30° C. and progress of the reaction was monitored by Thin Layer Chromatography (TLC) (ethyl acetate:hexane 1:1). After complete consumption of starting material the reaction mixture was filtered through celite bed and the residue was washed with methanol (2×10 mL). The solvent from combined filtrate was evaporated under reduced pressure to obtain 1-tert-butyl 2-methyl (2S,4R)-4-methylpyrrolidine-1, 2-dicarboxylate (IXa) (2.5 g, 60.8%).

Analysis:
Mass: 244.9 (M+H) for M.W: 243.31; M.F: $C_{12}H_{21}NO_4$;
$^1$H-NMR: (400 MHz, CDCl$_3$): δ 3.73 (s, 3H), 3.48 (s, 1H), 3.01-2.96 (m, 1H), 2.41-2.36 (m, 1H), 2.26-2.21 (m, 1H), 1.81-1.79 (m, 1H), 1.59-1.51 (m, 1H), 1.40 (s, 9H), 1.06 (s, 3H).

Step-4: Synthesis of tert-butyl (2S,4R)-2-(hydroxymethyl)-4-methylpyrrolidine-1-carboxylate (Xa)

To a clean dry flask Lithium aluminium hydride (0.849 g, 22.36 mmoles) was added under argon atmosphere. It was cooled up to −10° C. and tetrahydrofuran (25 mL) was added through addition funnel slowly. After stirring for 0.5 hour a solution of 1-tert-butyl 2-methyl (2S,4R)-4-methylpyrrolidine-1,2-dicarboxylate (IXa) (4.94 g, 20.33 mmoles) in tetrahydrofuran (25 mL) was added to the mixture drop-wise. The reaction was monitored by Thin Layer Chromatography (TLC) (ethyl acetate:hexane 1:4). After complete consumption of starting material, wet sodium sulfate was added slowly. The reaction mass was stirred at room temperature for four hours and filter through hyflo bed. The residue was washed with ethyl acetate (50 mL). The filtrate was evaporated under reduced pressure to remove all solvents. The concentrated mass was again diluted with ethyl acetate (50 mL) and the solution washed with saturated brine (20 mL). The organic layer was dried over sodium sulfate and evaporated under reduced pressure over rotavapor to obtain yellowish residue. The residue was dried in high vacuum to obtain tert-butyl (2S,4R)-2-(hydroxymethyl)-4-methylpyrrolidine-1-carboxylate (Xa) (3.8 g, 87%) and used as such in next reaction without further purification.

Analysis:
Mass: 215.9 (M+H) for M.W: 215.29; M.F: $C_{11}H_{21}NO_3$;
$^1$H-NMR: (500 MHz, CDCl$_3$): δ 4.55 (bs, 1H), 4.06 (bs, 1H), 3.63-3.60 (m, 2H), 3.48-3.46 (m, 1H), 2.97-2.93 (m, 1H), 2.29-2.25 (m, 1H), 1.69-1.64 (m, 2H), 1.47 (s, 9H), 1.02 (d, J=5 Hz, 3H).

Step-5: Synthesis of tert-butyl (2S,4R)-2-{[(1,3-dioxo-1,3-dihydro-2H-isoindol-2-yl)oxy]methyl}-4-methylpyrrolidine-1-carboxylate (XIa)

Diisopropylazodicarboxylate (4.2 mL, 21.20 mmol) was added to a solution of tetrahydrofuran (40 mL) containing tert-butyl (2S,4R)-2-(hydroxymethyl)-4-methylpyrrolidine-1-carboxylate (Xa) (3.8 g, 17.67 mmol), triphenylphosphine (5.55 g, 21.20 mmol), and N-hydroxy phthalimide (2.88 g, 17.67 mmol), under stirring, at room temperature (exothermic reaction, temperature controlled by ice water). After the addition, stirring continued for 4 hours at room temperature. Thin Layer Chromatography (TLC) at this stage indicates completion of reaction. The resulting mixture was then concentrated under reduced pressure to yield oily residue, which was purified by column chromatography using silica gel (60-120 mesh size). Elution with a v/v ethyl acetate: hexane (1:3) mixture as an eluent and evaporation of the combined fractions gave tert-butyl (2S,4R)-2-{[(1,3-dioxo-1,3-dihydro-2H-isoindol-2-yl)oxy]methyl}-4-methylpyrrolidine-1-carboxylate (XIa) (5.96 g, 92%), as an oil.

Analysis:
Mass: 361.2 (M+H) for M.W: 360.40; M.F: $C_{19}H_{24}N_2O_5$;
$^1$H-NMR: (400 MHz, CDCl$_3$): δ 7.84-7.75 (m, 4H), 4.38-4.30 (m, 1H), 4.17-3.95 (m, 2H), 3.56-3.49 (m, 1H), 2.92-2.83 (m, 1H), 2.43-2.38 (m, 2H), 1.74-1.69 (m, 1H), 1.40 (s, 9H), 1.09 (d, J=8 Hz, 3H).

Step-6: Synthesis of tert-butyl (2S,4R)-2-[(aminooxy)methyl]-4-methylpyrrolidine-1-carboxylate (XIIa)

Hydrazine hydrate (1.24 mL, 24.83 mmol) was added to the solution of tert-butyl (2S,4R)-2-{[(1,3-dioxo-1,3-dihydro-2H-isoindol-2-yl)oxy]methyl}-4-methylpyrrolidine-1-carboxylate (XIa) (5.96 g, 16.55 mmol) in dichloromethane (90 mL), under stirring, at room temperature. Stirring was continued further for 2 hour and the reaction was monitored by Thin Layer Chromatography (TLC) (ethyl acetate:hexane 1:3). After complete consumption of starting material the volatiles were removed under reduced pressure to obtain a yellowish residue. The residue was dried under reduced pressure (4 mmHg) to obtain tert-butyl (2S,4R)-2-[(aminooxy)methyl]-4-methylpyrrolidine-1-carboxylate (XIIa) (3.1 g, 82%) and used as such in the next reaction without further purification.

Analysis:
Mass: 229.7 (M−H) for M.W: 230.30; M.F: $C_{11}H_{22}N_2O_3$;

Step-7: Synthesis of (2S,5R)-6-benzyloxy-N-{[(2S,4R)-4-methylpyrrolidin-1-tertbutylcarboxylate]methoxy}-7-oxo-1,6-diazabicyclo[3.2.1]octane-2-carboxamide (XIVa)

N-(3-dimethylaminopropyl)-N'-ethylcarbodiimide hydrochloride (EDC.HCl, 3.86 g, 20.21 mmol), N-methylmorpholine (NMM, 1.83 mL, 13.47 mmol) and 1-Hydrxybenzotriazole (HOBT, 1.82 g, 13.47 mmol) were added successively to a stirred solution of sodium salt of (2S,5R)-6-benzyloxy-7-oxo-1,6-diazabicyclo[3.2.1]octane-2-carboxylic acid (XIII) (4.02 g, 13.47 mmol) in dimethylformamide (DMF, 40 ml) at 0° C. Compound (XIII) was prepared using the procedure disclosed in International Patent Application No PCT/IB2013/059264. To this cooled solution was further added a solution of compound (XIIa) (3.1 g, 13.47 mmol) in dimethylformamide (15 ml) at 0° C. and the stirring was continued further for 16 hours at room temperature. The reaction mixture was poured into cold water (1 L) while stirring. The separated solid was filtered and further purified by column chromatography using silica gel (60-120 mesh). Elution with a v/v mixture of ethyl acetate:hexane (1:3) and evaporation of the solvent from the combined fractions gave the compound (XIVa) (5.06 g, 77%) as a white solid.

Analysis:
Mass: 487.3 (M−H) for M.W: 488.59; M.F: $C_{25}H_{36}N_4O_6$;
$^1$H-NMR: (400 MHz, CDCl$_3$): δ 10.22 (bs, 1H), 7.43-7.37 (m, 5H), 5.06 (d, J=12.0 Hz, 1H), 4.90 (d, J=12.0 Hz, 1H), 4.14-3.73 (m, 4H), 3.49-3.45 (m, 1H), 3.30-2.27 (m, 1H), 3.05-3.02 (m, 1H), 2.89-2.83 (m, 2H), 2.31-2.27 (m, 2H), 2.05-1.99 (m, 2H), 1.84-1.80 (m, 2H), 1.67-1.64 (m, 1H), 1.45 (s, 9H), 1.04 (d, J=8 Hz, 3H).

Step-8: Synthesis of (2S,5R)-6-hydroxy-N-{[(2S, 4R)-4-methylpyrrolidin-1-tertbutylcarboxylate]methoxy}-7-oxo-1,6-diazabicyclo[3.2.1]octane-2-carboxamide (XVa)

A solution of compound (XIVa) (5.06 g, 10.37 mmoles) in methanol (40 mL) containing 10% palladium on carbon (1.69 g) was hydrogenated at 50 psi pressure at 25-30° C. The progress of the reaction was monitored by Thin Layer Chromatography (TLC) (ethyl acetate:hexane 1:1). After complete consumption of the starting material the reaction mixture was filtered through celite bed and the residue was washed with fresh methanol (2×20 mL). The combined filtrate was concentrated under reduced pressure to obtain compound (XVa) (3.55 g, 86%). This was used as such for the next reaction.

Analysis:
Mass: 397.3 (M−H) for M.W: 398.46; M.F: $C_{18}H_{30}N_4O_6$;

Step-9: Synthesis of tetrabutyl ammonium salt of (2S,5R)-6-sulfooxy-N-{[(2S,4R)-4-methylpyrrolidin-1-tertbutylcarboxylate]methoxy}-7-oxo-1,6-diazabicyclo[3.2.1]octane-2-carboxamide (XVIa)

Triethylamine (2.43 mL, 17.83 mmol) followed by pyridine sulphur trioxide complex (2.13 g, 13.36 mmol) was added to a solution of (2S,5R)-6-hydroxy-N-{[(2S,4R)-4-methylpyrrolidin-1-tertbutylcarboxylate]methoxy}-7-oxo-1,6-diazabicyclo[3.2.1]octane-2-carboxamide (XVa) (3.55 g, 8.91 mmol) in dichloromethane (35 mL) under stirring and argon atmosphere, at 25° C. Stirring was continued for 16 hour at 25° C. TLC indicates the completion of the reaction. The resulting mixture was filtered under suction and the residue washed with dichloromethane (25 mL). The combined filtrate was concentrated under reduced pressure to obtain the product as oil. A 0.5 M potassium hydrogen phosphate (KH$_2$PO$_4$) solution (150 mL) was added to the residual oil and stirred 0.5 hour at 25° C. The solution was washed with ethyl acetate (2×40 mL). The aqueous reaction mixture was taken in a flask and tetrabutyl ammonium hydrogen sulfate (3.62 g, 10.69 mmol) was added to it under stirring. The reaction mixture was stirred for 0.5 hour and extracted with dichloromethane (2×70 mL). The dichloromethane extract was dried on anhydrous sodium sulfate and volatiles were removed under reduced pressure to obtain the crude product. This was purified by column chromatography using 60-120 mesh silica gel and elution v/v mixture of dichloromethane:methanol (10:1). The pure fractions were collected and the solvent evaporated to obtain tetrabutyl ammonium salt of (2S,5R)-6-sulfooxy-N-{[(2S,4R)-4-methylpyrrolidin-1-tertbutylcarboxylate]methoxy}-7-oxo-1,6-diazabicyclo[3.2.1]octane-2-carboxamide (XVIa) (5.4 g, 83%).

Analysis:
Mass: 477.3 (M−H) for M.W: 719.99; M.F: $C_{34}H_{65}N_5O_9S$;
$^1$H-NMR: (400 MHz, CDCl$_3$): δ 10.27 (s, 1H), 4.35 (s, 1H), 4.16-4.15 (m, 1H), 4.01-3.93 (m, 2H), 3.91-3.79

(m, 1H), 3.76-3.74 (m, 1H), 3.48-3.37 (m, 1H), 3.32-3.28 (m, 8H), 2.92-2.88 (m, 2H), 2.33-2.31 (m, 2H), 2.20-2.16 (m, 1H), 1.92-1.84 (m, 1H), 1.68-1.65 (m, 12H), 1.48-1.42 (m, 16H), 1.06-1.01 (m, 15H)

Step-10: Synthesis of (2S,5R)—N-{[(2S,4R)-4-methylpyrrolidin-2-yl]methyloxy}-7-oxo-6-(sulfooxy)-1,6-diazabicyclo[3.2.1]octane-2-carboxamide (Ia)

Compound (XVIa) (5.4 g, 7.4 mmol) was dissolved in dichloromethane (32 ml) and the solution was cooled to −15° C. Trifluoroacetic acid (21.6 ml) was added drop-wise to the solution at −10° to −15° C. The reaction was monitored by ES-MS analysis. The temperature of the solution was maintained at −10 to −5° C. for 1 hour. After completion of the reaction, hexane (250 ml) was added to the reaction mixture. The hexane layer was decanted and the oily residue was washed thoroughly by hexane (150 ml) and diethyl ether (250 ml). The solid residue formed was further washed with diethyl ether, acetonitrile and dichloromethane (80 ml each). The residue was dried under reduced pressure to obtain the product as a white solid, which was recrystallized using a mixture of isopropanol and water (7:1) to obtain the compound of formula (Ia) as a white solid (2.05 g, yield: 73%).

Analysis:
Mass: 377.0 (M−H) for M.W: 378.41; M.F: $C_{13}H_{22}N_4O_7S$;
$^1$H-NMR: (500 MHz, DMSO-d$_6$): δ11.66 (s, 1H), 8.87 (broad s, 2H), 4.05-3.91 (m, 4H), 3.83 (d, J=5 Hz, 1H), 3.38-3.36 (m, 1H), 3.05-2.96 (m, 2H), 2.75 (dd, J=20 Hz, 10 Hz, 1H), 2.38-2.34 (m, 1H), 2.05-2.02 (m, 1H), 1.92-1.82 (m, 2H), 1.77-1.65 (m, 3H), 1.03 (d, J=5 Hz, 3H).
Melting Point: 172 to 174° C. (decomposition)

Example 2

(2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide (Ib)

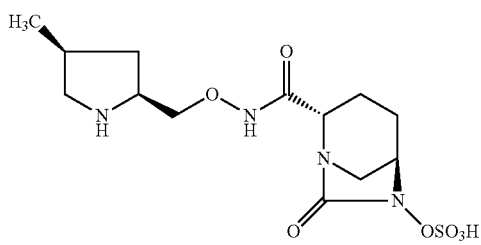

Compound of Formula (Ib) was prepared according to the procedure described in Example 1, starting with 1-tert-butyl-2-methyl (2S,4S)-4-methyl pyrrolidine-1, 2-dicarboxylate (compound (Xb)), in about 23% overall yield.

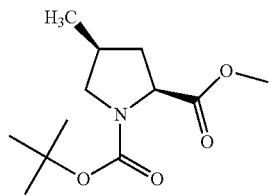

Analysis:
Mass: 377.0 (M−H) for M.W: 378.41; M.F: $C_{13}H_{22}N_4O_7S$;
$^1$H-NMR: (500 MHz, DMSO-d$_6$): δ 11.74 (s, 1H), 8.82 (broad s, 2H), 4.01-3.92 (m, 3H), 3.82-3.77 (m, 2H), 3.61-3.57 (m, 1H), 3.33 (dd, J=15 Hz, 10 Hz, 1H), 3.07-3.02 (m, 1H), 2.97-2.94 (m, 1H), 2.72 (t, J=15 Hz, 1H), 2.43-2.31 (m, 1H), 2.19-2.13 (m, 1H), 2.06-2.01 (m, 1H), 1.90-1.85 (m, 1H), 1.75-1.63 (m, 3H), 1.03 (d, J=5 Hz, 3H).

Example 3

(2S,5R)—N-{[(2R,4S)-4-Methyl-pyrrolidin-2-yl]methyloxy}-7-oxo-6-(sulfooxy)-1,6-diazabicyclo[3.2.1]octane-2-carboxamide (Ic)

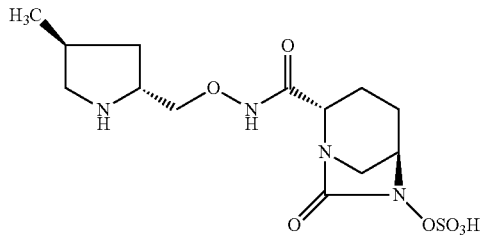

Compound of Formula (Ic) was prepared according to the procedure described in Example 1, starting with 1-tert-butyl-2-methyl (2R,4S)-4-methyl pyrrolidine-1, 2-dicarboxylate (compound (Xc)), in about 16.4% overall yield.

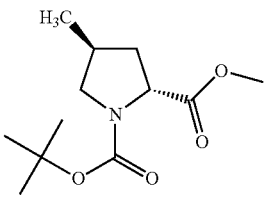

Analysis:
Mass: 377.0 (M−H) for M.W: 378.41; M.F: $C_{13}H_{22}N_4O_7S$;
$^1$H-NMR: (500 MHz, DMSO-d$_6$): δ 11.72 (s, 1H), 8.96 (bs, 1H), 8.70 (bs, 1H), 4.03-3.80 (m, 3H), 3.81-3.80 (d, 1H), 3.43-3.37 (m, 2H), 3.05-2.98 (m, 2H), 2.75-2.73 (m, 1H), 2.38-2.33 (m, 1H), 2.08-2.07 (d, 2H), 1.89-1.82 (m, 2H), 1.71-1.65 (m, 2H), 1.03-1.02 (d, 3H).

Example 4

(2S,5R)—N-{[(2R,4R)-4-Methyl-pyrrolidin-2-yl]methyloxy}-7-oxo-6-(sulfooxy)-1,6-diazabicyclo[3.2.1]octane-2-carboxamide (Id)

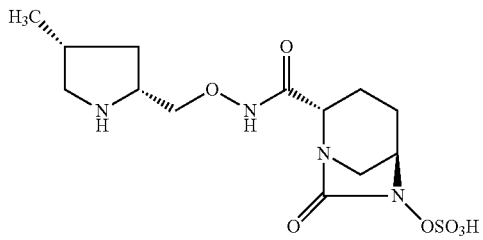

(Id)

Compound of Formula (Id) was prepared according to the procedure described in Example 1, starting with 1-tert-butyl-2-methyl (2R,4R)-4-methyl pyrrolidine-1, 2-dicarboxylate (compound (Xd)), in about 20% overall yield.

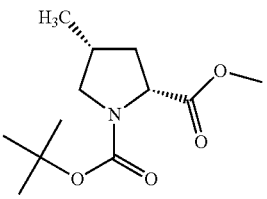

(Xd)

Analysis:
Mass: 377.0 (M–H) for M.W: 378.41; M.F: $C_{13}H_{22}N_4O_7S$;
$^1$H-NMR: (500 MHz, DMSO-$d_6$): δ 11.73 (s, 1H), 8.88 (bs, 1H), 8.75 (bs, 1H), 4.03-3.97 (m, 2H), 3.81-3.80 (d, 2H), 3.35-3.34 (m, 1H), 3.03-2.99 (m, 2H), 2.75-2.71 (m, 1H), 2.30-2.29 (m, 1H), 2.19-2.17 (m, 1H), 2.08 (s, 1H), 2.04-2.02 (m, 1H), 1.90-1.89 (m, 1H), 1.71-1.70 (m, 2H), 1.23-1.21 (m, 1H), 1.04-1.03 (d, 3H).

The compounds of Examples 5 to 10 (Table 1) were prepared by following the procedures described in Example 1 and following the Scheme 1 and/or Scheme 2,

TABLE 1

| Sr. | Compound of Formula (I) | Analysis |
|---|---|---|
| 5 | (structure with HO-pyrrolidine) | $^1$H-NMR: (400 MHz, DMSO-$d_6$): δ 11.73 (s, 1 H), 8.89 (bs, 1 H), 8.71 (bs, 1 H), 4.86 (bs, 1 H), 4.03-3.93 (m, 3 H), 3.84-3.79 (m, 2 H), 3.43-3.28 (m, 4 H), 3.06-2.96 (m, 3 H), 2.44-1.41 (m, 1 H), 2.13-2.03 (m, 2 H), 1.92-1.88 (m, 1 H), 1.75-1.68 (m, 2 H). M.F: $C_{13}H_{22}N_4O_8S$; M.W: 394.41; Mass 393.40 (M – H) |
| 6 | (structure with HO-pyrrolidine) | $^1$H-NMR: (400 MHz, DMSO-$d_6$): δ 11.75 (s, 1 H), 8.93 (bs, 1 H), 8.70 (bs, 1 H), 4.83 (bs, 1 H), 4.08-3.89 (m, 5 H), 3.44-3.32 (m, 3 H), 3.18-2.96 (m, 3 H), 2.50-2.43 (m, 1 H), 2.05-1.64 (m, 6 H). M.F. $C_{13}H_{22}N_4O_7S$; M.W: 394.40; Mass: 393.3 (M – H) |
| 7 | (structure with HO-pyrrolidine) | $^1$H-NMR: (500 MHz, DMSO-$d_6$): δ 11.73 (s, 1 H), 8.91 (bs, 1H), 8.70 (bs, 1H), 4.90-4.88 (t, 1H, J = 5 Hz), 4.03-4.00 (m, 2H), 3.94-3.90 (m, 1 H), 3.85-3.80 (m, 2H), 3.42-3.32 (m, 3H), 3.05-3.03 (m, 1H), 2.99-2.97 (m, 2H), 2.45-2.43 (m, 1H), 2.04-2.02 (m, 1H), 1.90-1.81 (m, 2H), 1.74-1.70 (m, 3H). M.F. $C_{13}H_{22}N_4O_7S$; M.W: 394.40; Mass: 393.3 (M – H) |
| 8 | (structure with HO-pyrrolidine) | $^1$H-NMR: (500 MHz, DMSO-$d_6$): δ 11.71 (s, 1H), 8.88 (bs, 1H), 8.69 (bs, 1H), 4.86 (s, 1H), 4.03-3.93 (m, 2H), 3.81-3.80 (m, 2H), 3.43-3.38 (m, 2H), 3.29-3.27 (m, 1H), 3.06-2.98 (m, 3H), 2.45-2.41 (m, 1H), 2.12-2.09 (m, 1H), 2.04-2.02 (m, 1H), 1.90-1.89 (m, 1 H), 1.73-1.68 (m, 2H), 1.36-1.30 (m, 2H). M.F. $C_{13}H_{22}N_4O_7S$; M.W: 394.40; Mass: 393.3 (M – H) |
| 9 | (structure with H2N-pyrrolidine, •CF3COOH) | $^1$H-NMR: (500 MHz, DMSO-$d_6$): δ 11.81 (bs, 1H), 9.03 (bs, 2H), 7.93 (bs, 2H), 4.03-3.98 (m, 3H, J = 5 Hz), 3.83-3.82 (m, 1H), 3.46-3.43 (m, 1 H), 3.03-2.92 (m, 5H), 2.51-2.50 (m, 1H), 2.27-2.23 (m, 1H), 2.08-2.03 (m, 2H), 1.88-1.86 (m, 1H), 1.72-1.70 (m, 2H), 1.42-1.36 (m, 2H). M.F: $C_{13}H_{23}N_5O_7S \cdot C_2HF_3O_2$; M.W: 507.44; Mass: 392.1 (M – H) |

TABLE 1-continued

| Sr. | Compound of Formula (I) | Analysis |
|---|---|---|
| 10 | 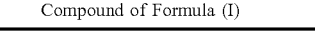 | $^1$H-NMR: (500 MHz, DMSO-d$_6$): δ 11.78 (s, 1H), 9.05-8.82 (bs, 2H), 4.51-4.40 (d sym. m, J = 50 Hz, HF coupling 2H,), 4.03-4.02 (m, 2H), 4.01-4.00 (m, 1H), 3.88-3.87 (m, 1H), 3.83 (m, 1H), 3.45-3.44 (m, 1H), 3.04-2.99 (m, 2H), 2.75-2.71 (m, 1H), 2.07-2.02 (m, 1H), 1.88-1.84 (m, 3H), 1.72-1.70 (m, 2H). M.F: C$_{13}$H$_{21}$FN$_4$O$_7$S; M.W: 396.40; Mass: 395.0 (M − H) |

BIOLOGICAL ACTIVITY

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations, (Clinical and Laboratory Standards Institute (CLSI), Performance Standards for Antimicrobial Susceptibility Testing, 20$^{th}$ Informational Supplement, M07-A9, Volume 32, No. 2, 2012). Molten Mueller Hinton Agar (MHA) (BD, USA) containing serial dilutions of each antibacterial agent were poured on to the plates and allowed to solidify. Appropriate suspensions from the freshly grown cultures were prepared in normal saline so that about 10$^4$ CFU/spot of the organism was delivered on to the drug containing agar plates using automated multipoint inoculator (Mast, UK).

The plates were incubated in Biochemical oxygen demand (BOD) incubator at 37° C. for 18 hours and then examined for growth. MICs were read as the lowest concentration of drug that completely inhibited bacterial growth. The Table 2 depicts the antibacterial activity profile of compounds according to present invention against various multidrug resistant bacterial strains.

The antibacterial activity of compounds according to the invention was also investigated in combination with several antibacterial agents. For example, antibacterial activity of the representative compounds of Formula (I) (Example 1 and Example 2) in combination with Ceftazidime and Cefixime are summarized in Table 3.

As can be seen from Table 3, Ceftazidime, Cefixime and representative compounds of Formula (I) (Example 1 and Example 2) when used alone, did not exhibit significant antibacterial activity. However, surprisingly the representative compounds of Formula (I) (Example 1 and Example 2) in combination with Ceftazidime and Cefixime exhibited unusual and unexpected synergistic antibacterial effect against highly resistant bacterial strains.

TABLE 2

Antibacterial activity of representative compounds according to invention (expressed as MICs (mcg/ml))

| Compounds | KP ATCC 700603 | E. Coli 13351 | E. Coli 13352 | E. Coli 13353 | E. Coli M 36 | E. Coli 7 MP | E. Coli M 49 | E. Coli M 50 | E. Coli M 138 | E. Coli S 18 | K. pneumoniae H 521 | K. pneumoniae H 522 | K. pneumoniae H 523 | K. pneumoniae H 525 |
|---|---|---|---|---|---|---|---|---|---|---|---|---|---|---|
| Example 1 | >32 | 1 | 1 | 0.5 | 0.5 | 1 | 4 | 0.5 | 0.5 | 1 | 1 | 1 | 0.5 | 0.5 |
| Example 2 | >32 | 1 | 1 | 0.5 | 0.5 | 2 | 4 | 1 | 1 | 1 | 2 | 1 | 1 | 1 |
| Example 3 | >32 | 1 | 1 | 0.5 | 0.5 | 2 | 4 | 0.5 | 0.5 | 1 | 1 | 1 | 0.5 | 0.5 |
| Example 4 | >32 | 1 | 2 | 1 | 0.5 | 2 | 4 | 1 | 1 | 1 | 2 | 2 | 2 | 2 |
| Example 5 | >32 | 1 | 2 | 1 | 1 | 2 | 4 | 1 | 1 | 1 | 1 | 1 | 1 | 1 |
| Example 6 | >32 | 1 | 2 | 1 | 1 | 2 | 4 | 1 | 1 | 1 | 2 | 2 | 2 | 1 |
| Example 7 | >32 | 1 | 2 | 1 | 1 | 2 | 4 | 1 | 1 | 1 | 2 | 2 | 1 | 1 |
| Example 8 | >32 | 2 | 4 | 1 | 1 | 4 | 4 | 1 | 1 | 2 | 4 | 8 | 1 | 1 |
| Example 9 | >32 | 4 | 4 | 2 | 2 | 8 | 4 | 2 | 4 | 2 | 4 | 4 | 2 | 2 |
| Example 10 | >32 | 1 | 2 | 1 | 1 | 2 | 4 | 1 | 1 | 1 | 2 | 2 | 2 | 2 |

TABLE 3

Antibacterial activity of Ceftazidime and Cefixime in presence of representative compounds of the invention against various Multi Drug Resistant (MDR) Gram negative strains.

| | | | | MIC (mg/L) | | | | | | |
|---|---|---|---|---|---|---|---|---|---|---|
| Sr. | Organism | Strain | Beta lactamase | Ceftazidime | Cefixime | Example 1 | Example 2 | Ceftazidime + Example 1 | Ceftazidime + Example 2 | Cefixime + Example 1 | Cefixime + Example 2 |
| 1 | K. pneumoniae | B 77 | NDM, ESBL | >32 | >32 | >32 | >32 | 0.5 | 2 | 1 | 2 |
| 2 | K. pneumoniae | B 88 | NDM, ESBL | >32 | >32 | >32 | >32 | 0.5 | 1 | 2 | 1 |
| 3 | K. pneumoniae | NCTC 13443 | NDM, ESBL | >32 | >32 | >32 | >32 | 4 | 4 | 4 | 4 |
| 4 | K. pneumoniae | S 465 | OXA-181, ESBL | >32 | >32 | >32 | >32 | 1 | 2 | 1 | 2 |

TABLE 3-continued

Antibacterial activity of Ceftazidime and Cefixime in presence of representative compounds of the invention against various Multi Drug Resistant (MDR) Gram negative strains.

| Sr. | Organism | Strain | Beta lactamase | Ceftazidime | Cefixime | Example 1 | Example 2 | Ceftazidime + Example 1 | Ceftazidime + Example 2 | Cefixime + Example 1 | Cefixime + Example 2 |
|---|---|---|---|---|---|---|---|---|---|---|---|
| 5 | K. pneumoniae | NCTC 13439 | VIM-1 | >32 | >32 | >32 | >32 | 0.5 | 1 | 1 | 1 |

We claim:

1. A compound of Formula (I), or a stereoisomer or a pharmaceutically acceptable salt thereof:

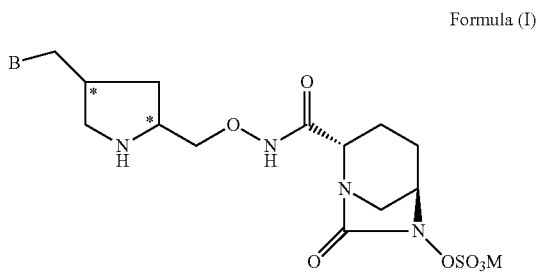

Formula (I)

wherein:
B is selected from:
(a) hydrogen,
(b) halogen,
(c) $C_1$-$C_6$ alkyl,
(d) $OR_1$,
(e) $NR_1R_2$,
(f) SH,
(g) $SR_1$,
(h) $SOR_1$,
(i) $SO_2R_1$,
(j) CHO,
(k) $COOR_1$,
(l) $CONR_1R_2$,
(m) CN,
(n) heteroaryl,
(o) heterocycloalkyl, or
(P) NHC(=NH)NH$_2$;

$R_1$ and $R_2$ are each independently:
(a) hydrogen,
(b) $C_1$-$C_6$ alkyl, optionally substituted with one or more substituents independently selected from CN, halogen, OH, NH$_2$, COOH, CONH$_2$, SH, cycloalkyl, heterocycloalkyl, aryl, or heteroaryl,
(c) three to seven membered cycloalkyl, optionally substituted with one or more substituents independently selected from CN, halogen, OH, NH$_2$, COOH, CONH$_2$, or SH,
(d) three to seven membered heterocycloalkyl, optionally substituted with one or more substituents independently selected from CN, halogen, OH, NH$_2$, COOH, CONH$_2$, or SH,
(e) six to fourteen membered aryl, optionally substituted with one or more substituents independently selected from CN, halogen, OH, NH$_2$, COOH, CONH$_2$, or SH, or
(f) five to fourteen membered heteroaryl, optionally substituted with one or more substituents independently selected from CN, halogen, OH, NH$_2$, COOH, CONH$_2$, SH;

M is selected from:
(a) hydrogen,
(b) $C_1$-$C_6$ alkyl, or
(c) a pharmaceutically accepted salt forming cation independently selected from Na, K, or Ca.

2. The compound according to claim 1, selected from:
(2S,5R)—N-{[(2S,4R)-4-Methyl-pyrrolidin-2-yl]methyloxy}-7-oxo-6-(sulfooxy)-1,6-diazabicyclo[3.2.1]octane-2-carboxamide;
(2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide;
(2S,5R)—N-{[(2R,4S)-4-Methyl-pyrrolidin-2-yl]methyloxy}-7-oxo-6-(sulfooxy)-1,6-diazabicyclo[3.2.1]octane-2-carboxamide;
(2S,5R)—N-{[(2R,4R)-4-Methyl-pyrrolidin-2-yl]methyloxy}-7-oxo-6-(sulfooxy)-1,6-diazabicyclo[3.2.1]octane-2-carboxamide;
(2S,5R)—N-{[(2S,4R)-4-Hydroxymethyl-pyrrolidin-2-yl]methyloxy}-7-oxo-6-(sulfooxy)-1,6-diazabicyclo[3.2.1]octane-2-carboxamide;
2S,5R)—N-{[(2S,4S)-4-Hydroxymethy-pyrrolidin-2-yl]methyloxy}-7-oxo-6-(sulfooxy)-1,6-diazabicyclo[3.2.1]octane-2-carboxamide;
(2S,5R)—N-{[(2R,4S)-4-Hydroxymethyl-pyrrolidin-2-yl]methyloxy}-7-oxo-6-(sulfooxy)-1,6-diazabicyclo[3.2.1]octane-2-carboxamide;
(2S,5R)—N-{[(2R,4R)-4-Hydroxymethy-pyrrolidin-2-yl]methyloxy}-7-oxo-6-(sulfooxy)-1,6-diazabicyclo[3.2.1]octane-2-carboxamide;
(2S,5R)—N-{[(2S,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;
(2S,5R)—N-{[(2S,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;
(2S,5R)—N-{[(2R,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;
(2S,5R)—N-{[(2R,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;
(2S,5R)—N-{[(2S,4R)-4-Cyanomethyl-pyrrolidin-2-yl]methyloxy}-7-oxo-6-(sulfooxy)-1,6-diazabicyclo[3.2.1]octane-2-carboxamide;
(2S,5R)—N-{[(2S,4S)-4-Cyanomethy-pyrrolidin-2-yl]methyloxy}-7-oxo-6-(sulfooxy)-1,6-diazabicyclo[3.2.1]octane-2-carboxamide;
(2S,5R)—N-{[(2R,4S)-4-Cyanomethyl-pyrrolidin-2-yl]methyloxy}-7-oxo-6-(sulfooxy)-1,6-diazabicyclo[3.2.1]octane-2-carboxamide;
(2S,5R)—N-{[(2R,4R)-4-Cyanomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Fluoromethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Chloromethyl-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Mercaptomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Piperidin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Piperazin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-1,2,4,triazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-(2H-tetrazoyl-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;

(2S,5R)—N-{[(2S,4S)-4-Carbamimidomethyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-Carbamimidomethyl-pyrrolidin-2-yl]methyloxy}-7-oxo-6-(sulfooxy)-1,6-diazabicyclo[3.2.1]octane-2-carboxamide;

(2S,5R)—N-{[(2R,4S)-4-Carbamimidomethyl-pyrrolidin-2-yl]methyloxy}-7-oxo-6-(sulfooxy)-1,6-diazabicyclo[3.2.1]octane-2-carboxamide;

(2S,5R)—N-{[(2R,4R)-4-Carbamimidomethyl-pyrrolidin-2-yl]methyloxy}-7-oxo-6-(sulfooxy)-1,6-diazabicyclo[3.2.1]octane-2-carboxamide;

or a stereoisomer or a pharmaceutically acceptable salt thereof.

3. The compound according to claim 1, selected from:

Sodium salt of (2S,5R)—N-{[(2S,4R)-4-Methyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-Methyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Methyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Methyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Hydroxymethyl-pyrrolidin-2-yl]methyloxy}-7-oxo-6-(sulfooxy)-1,6-diazabicyclo[3.2.1]octane-2-carboxamide;

Sodium salt of 2S,5R)—N-{[(2S,4S)-4-Hydroxymethy-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Hydroxymethy-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Hydroxymethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;

Sodium salt of (2S,5R)—N-{[(2S,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;

Sodium salt of (2S,5R)—N-{[(2R,4S)-4-Aminomethyl-pyrrolidin-2-yl]methyloxy}-7-oxo-6-(sulfooxy)-1,6-diazabicyclo[3.2.1]octane-2-carboxamide trifluoroacetate salt;

Sodium salt of (2S,5R)—N-{[(2R,4R)-4-Aminomethyl-pyrrolidin-2-yl]methyloxy}-7-oxo-6-(sulfooxy)-1,6-diazabicyclo[3.2.1]octane-2-carboxamide trifluoroacetate salt;

Sodium salt of (2S,5R)—N-{[(2S,4R)-4-Cyanomethyl-pyrrolidin-2-yl]methyloxy}-7-oxo-6-(sulfooxy)-1,6-diazabicyclo[3.2.1]octane-2-carboxamide;

Sodium salt of 2S,5R)—N-{[(2S,4S)-4-Cyanomethy-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Cyanomethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Cyanomethy-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Fluoromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-Fluoromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Fluoromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Fluoromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Chloromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-Chloromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Chloromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Chloromethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-Mercaptomethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-Mercaptomethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-Mercaptomethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-Mercaptomethyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Aziridin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Aziridin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Azetidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Azetidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Pyrrolidin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Piperidin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Piperidin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Piperidin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Piperidin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Azepan-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Azepan-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Piperazin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Piperazin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4S)-4-(Piperazin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2R,4R)-4-(Piperazin-1-yl-methyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(Morpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(Thiomorpholin-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-Pyrrol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-imidazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-pyrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-1,2,3-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-1,2,4-triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-1,2,4,triazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(1H-tetrazol-1-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-(2H-tetrazoly-2-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-(2H-tetrazol-2-ylmethyl)-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4S)-4-Carbamimidomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2S,4R)-4-Carbamimidomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4S)-4-Carbamimidomethyl-pyrrolidin-2-yl]methyloxy}-7-oxo-6-(sulfooxy)-1,6-diazabicyclo[3.2.1]octane-2-carboxamide;
Sodium salt of (2S,5R)—N-{[(2R,4R)-4-Carbamimidomethyl-pyrrolidin-2-yl]methyloxy}-7-oxo-6-(sulfooxy)-1,6-diazabicyclo[3.2.1]octane-2-carboxamide;
or a stereoisomer.

4. The compound according to claim 1, selected from:
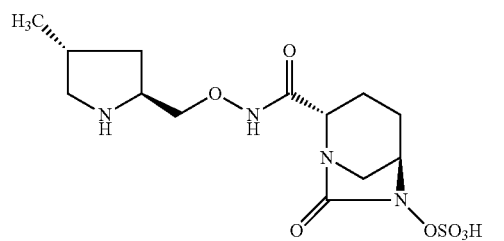
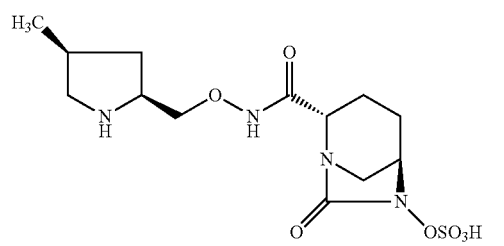
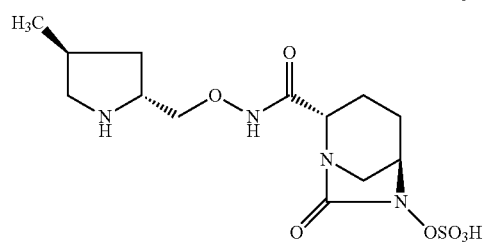
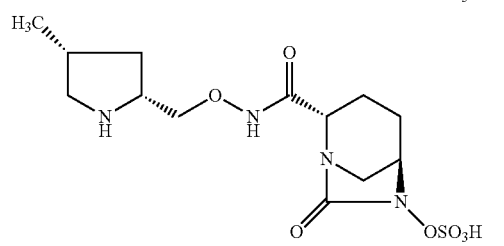
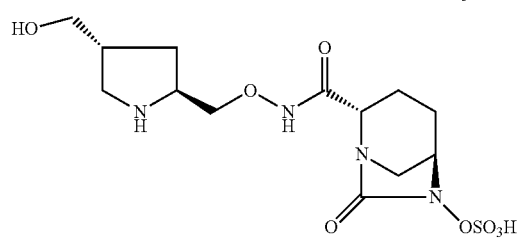
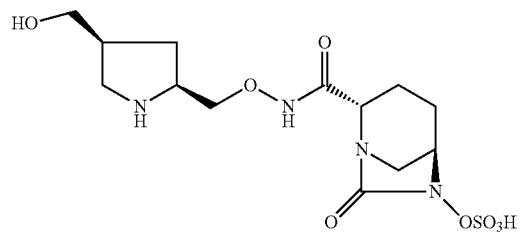
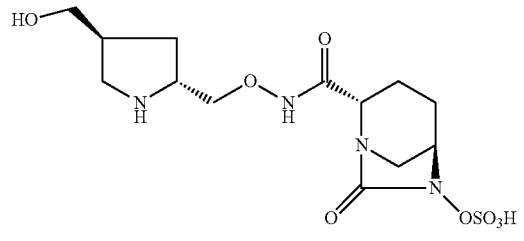
-continued
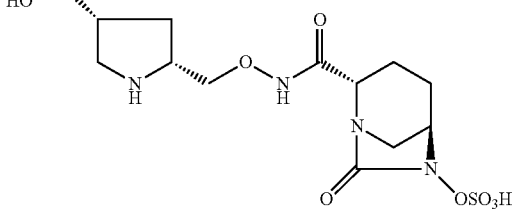
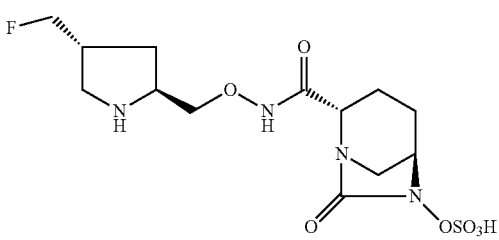
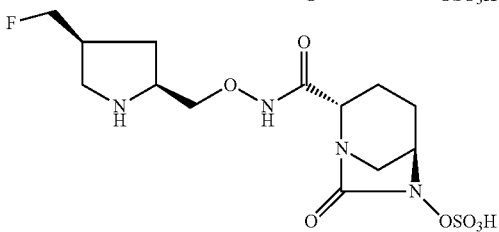
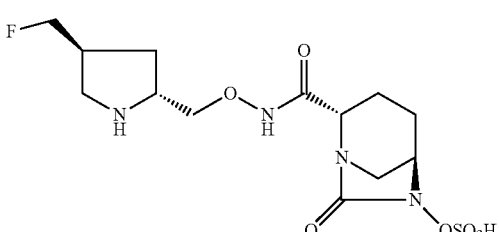
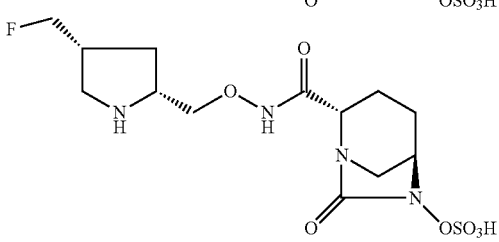
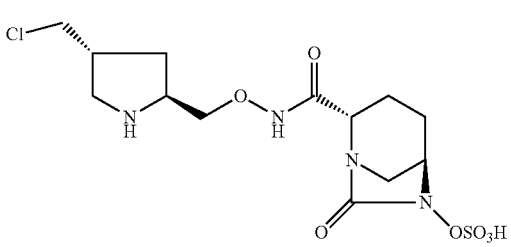
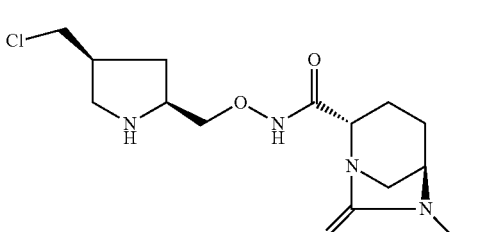

57
-continued
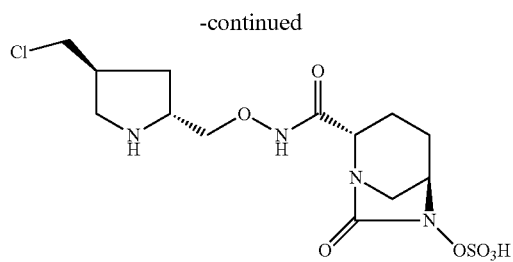
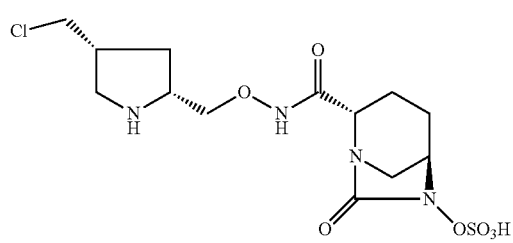
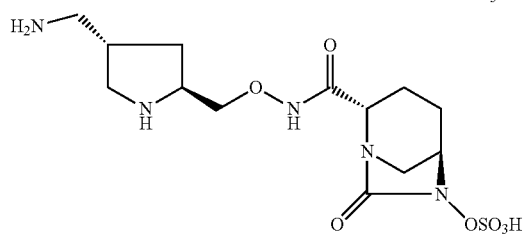
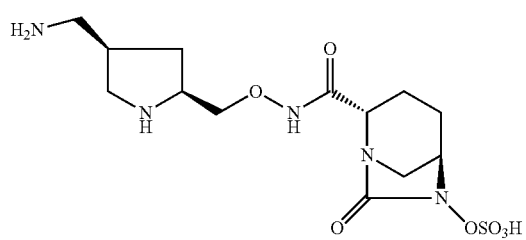
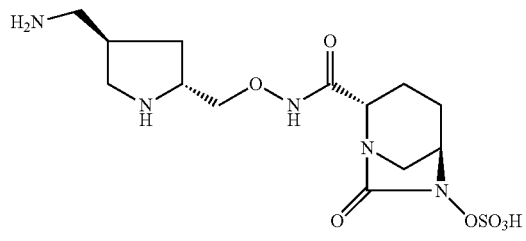
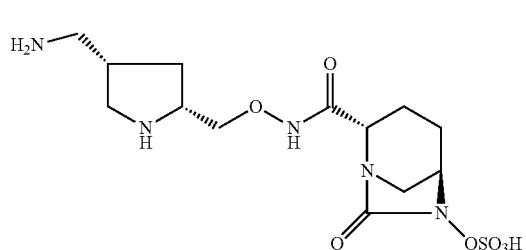
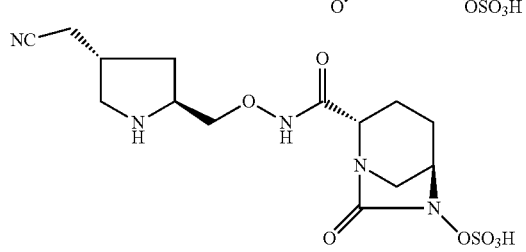
58
-continued
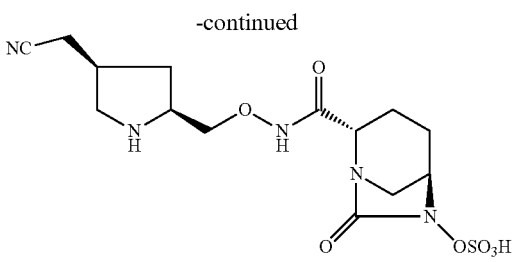
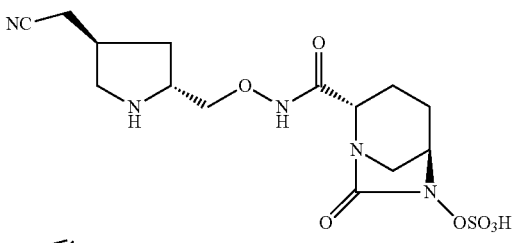
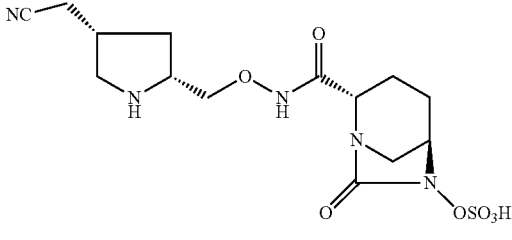
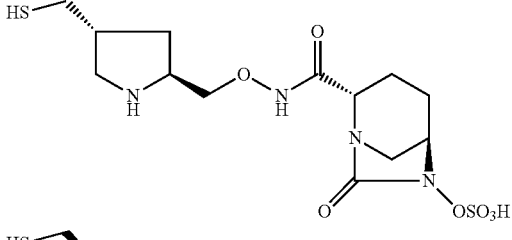
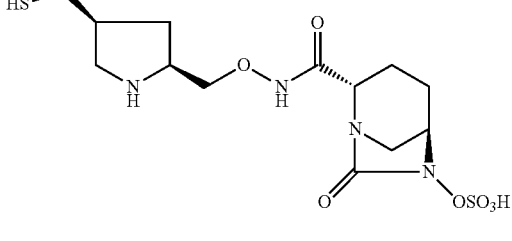
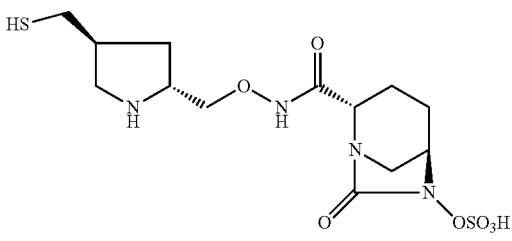
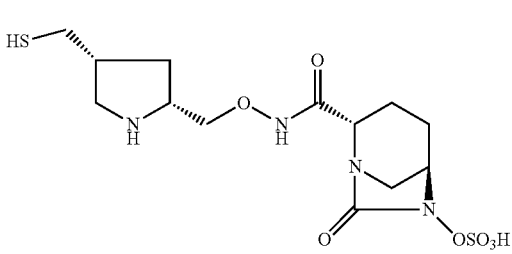

-continued

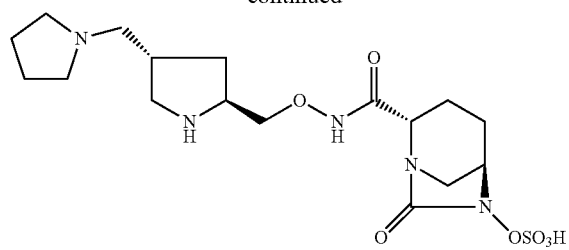
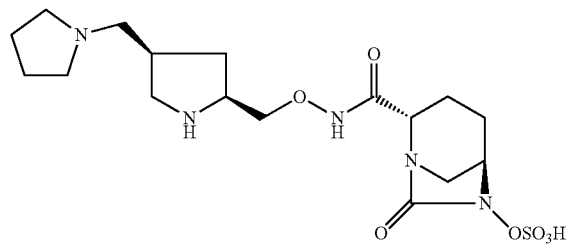
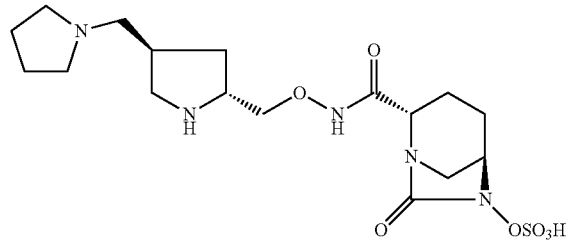
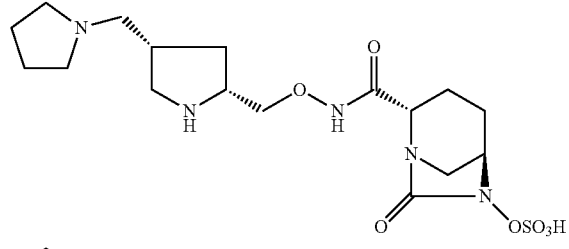
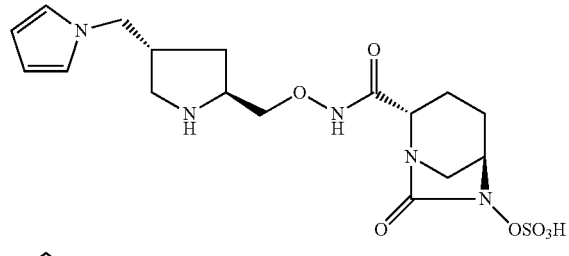
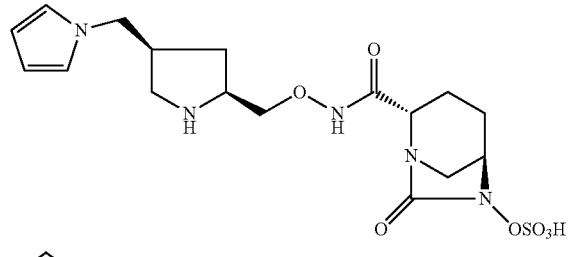
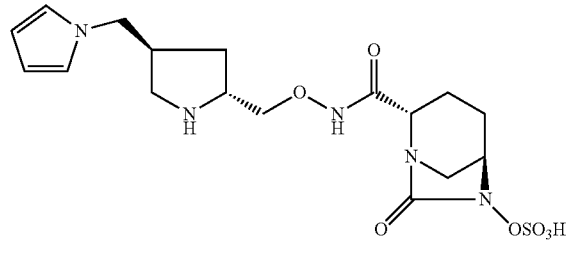

-continued

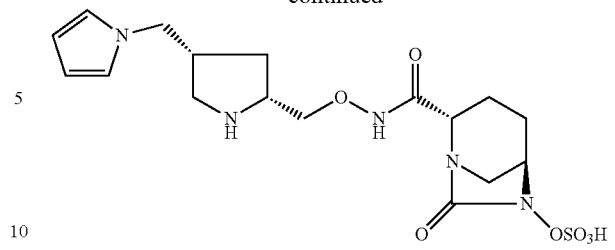
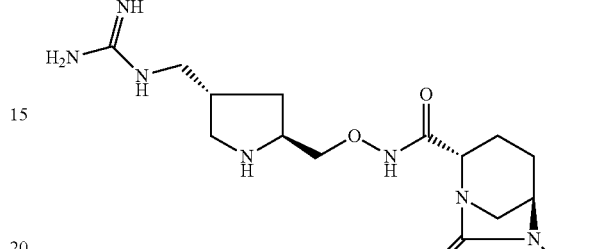
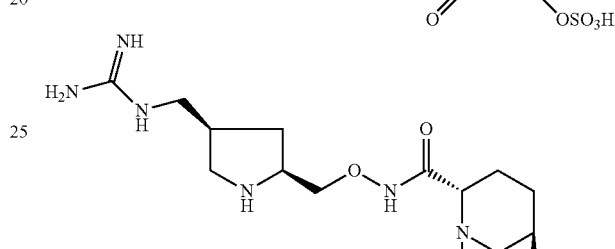
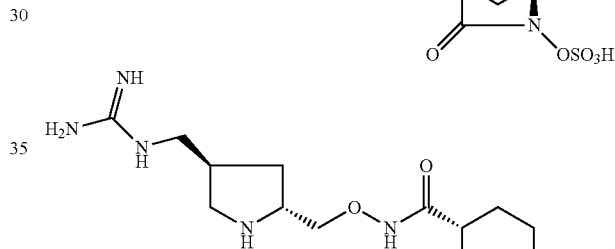
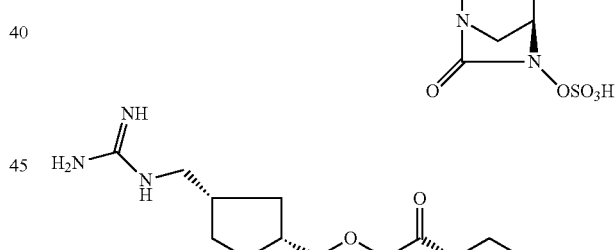
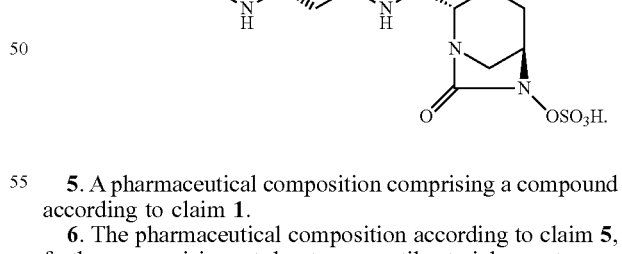

5. A pharmaceutical composition comprising a compound according to claim 1.

6. The pharmaceutical composition according to claim 5, further comprising at least one antibacterial agent or a pharmaceutically acceptable salt thereof.

7. The pharmaceutical composition according to claim 6, wherein the antibacterial agent is a beta-lactam antibacterial agent.

8. The pharmaceutical composition according to claim 6, wherein the antibacterial agent is at least one selected from a group consisting of Ansamycin, Carbacephem, Carbapenam, Carbapenem, Cephalosporin, Cephamycin, Cephem, Lincosamide, Lipopeptide, Macrolide, Ketolide, Monobactam, Nitrofuran, Oxacephem, Oxapenam, Oxazolidinone, Penam, Penem, Penicillin, Polypeptide, Quinolone, Sulfonamide, or Tetracycline antibacterial agents.

9. The pharmaceutical composition according to claim 6, wherein the antibacterial agent is at least one selected from a group consisting of cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefclidin, cefdaloxime, cefdinir, cefditoren, cefepime, cefetamet, cefixime, ceflupренam, cefmenoxime, cefmetazole, cefminox, cefodizime, cefonicid, cefoperazone, ceforanide, cefoselis, cefotaxime, cefotetan, cefotiam, cefovecin, cefoxitin, cefoxitin, cefozopran, cefpimizole, cefpiramide, cefpirome, cefpodoxime, cefprozil, cefquinome, cefradine, cefroxadine, cefsulodin, ceftaroline, ceftazidime, cefteram, ceftezole, ceftibuten, ceftiofur, ceftiolene, ceftizoxime, ceftobiprole, ceftolozane, ceftriaxone, cefuroxime, cefuzonam, cephaloridine, cephradine, cefiderocol, flomoxef, latamoxef, loracarbef, moxalactam, or a pharmaceutically acceptable salt thereof.

10. The pharmaceutical composition according to claim 6, wherein the antibacterial agent is at least one selected from a group consisting of cefaclor, cefadroxil, cefalexin, cefdinir, cefixime, cefpirome, cefpodoxime, cefprozil, cefradine, ceftibuten, cefuroxime, loracarbef, or a pharmaceutically acceptable salt thereof.

11. The pharmaceutical composition according to claim 6, wherein the antibacterial agent is at least one selected from a group consisting of ertapenem, doripenem, imipenem, meropenem, panipenem, biapenem, tebipenem, lenapenem, tomopenem, or a pharmaceutically acceptable salt thereof.

12. The pharmaceutical composition according to claim 6, wherein the antibacterial agent is at least one selected from a group consisting of cefpodoxime axetil, cefpodoxime proxetil, ceftibuten, cefuroxime, cefuroxime axetil, cefixime, or a pharmaceutically acceptable salt thereof.

13. A method for treating or preventing bacterial infection in a subject, said method comprising administering to said subject a compound according to claim 1.

14. A method for treating or preventing bacterial infection in a subject, said method comprising administering to said subject a pharmaceutical composition according to claim 5.

* * * * *